US011969046B2

(12) United States Patent
Lambert

(10) Patent No.: US 11,969,046 B2
(45) Date of Patent: Apr. 30, 2024

(54) PROTECTIVE APPAREL SYSTEM WITH A LENS ASSEMBLY

(71) Applicant: Stryker Corporation, Kalamazoo, MI (US)

(72) Inventor: Trevor Jonathan Lambert, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 688 days.

(21) Appl. No.: 17/255,630

(22) PCT Filed: Jun. 27, 2019

(86) PCT No.: PCT/US2019/039523
§ 371 (c)(1),
(2) Date: Dec. 23, 2020

(87) PCT Pub. No.: WO2020/006243
PCT Pub. Date: Jan. 2, 2020

(65) Prior Publication Data
US 2021/0259347 A1 Aug. 26, 2021

Related U.S. Application Data

(60) Provisional application No. 62/690,559, filed on Jun. 27, 2018.

(51) Int. Cl.
*A42B 3/04* (2006.01)
*A41D 13/11* (2006.01)
*A41D 13/12* (2006.01)

(52) U.S. Cl.
CPC .......... *A42B 3/044* (2013.01); *A41D 13/1161* (2013.01); *A41D 13/1218* (2013.01)

(58) Field of Classification Search
CPC ......... A42B 3/044; A42B 1/242; A42B 1/244; A41D 13/1184; A41D 13/1218;
(Continued)

(56) References Cited

U.S. PATENT DOCUMENTS

| 4,092,704 A * | 5/1978 | Malm | A42B 3/044 |
| | | | 362/105 |
| 4,199,802 A * | 4/1980 | Malm | A42B 3/044 |
| | | | 362/105 |

(Continued)

FOREIGN PATENT DOCUMENTS

| CN | 105093524 A | 11/2015 |
| EP | 2853169 A1 | 4/2015 |

(Continued)

OTHER PUBLICATIONS

English language abstract for CN 105093524 A extracted from espacenet.com database on Jul. 7, 2023, 2 pages.

(Continued)

*Primary Examiner* — Heather Mangine
(74) *Attorney, Agent, or Firm* — Howard & Howard Attorneys PLLC

(57) ABSTRACT

A protective apparel system for use with a surgical helmet having a headlamp and including a protective apparel apparatus comprising a surgical garment, wherein the garment defines a sterile barrier between the wearer and the environment. The system includes a lens assembly adjacent to the surgical garment on the environment side and configured to cooperate with a coupling member for use with the headlamp. The lens assembly may include a control member and a lens, wherein the control member is be manipulatable by a wearer. The control member may be configured wherein manipulation by the wearer may reposition the lens of the lens assembly to adjust the direction and/or intensity of the (Continued)

light from the headlamp without breaching the sterile barrier.

18 Claims, 16 Drawing Sheets

(58) Field of Classification Search
CPC ......... A62B 17/04; A61F 9/06; A61B 1/0692; G02B 27/0176; G02B 27/024
See application file for complete search history.

(56) References Cited

U.S. PATENT DOCUMENTS

| | | | |
|---|---|---|---|
| 4,238,709 A * | 12/1980 | Wallace | H05B 39/047 362/296.01 |
| 4,533,984 A * | 8/1985 | Gatton | F21V 23/0414 362/306 |
| 4,817,212 A * | 4/1989 | Benoit | A42B 1/244 362/106 |
| 5,301,372 A | 4/1994 | Matoba | |
| 5,341,513 A * | 8/1994 | Klein | A61F 9/02 128/857 |
| 5,630,412 A | 5/1997 | Dubruille et al. | |
| 5,711,033 A * | 1/1998 | Green | F04D 17/16 2/424 |
| 6,075,322 A * | 6/2000 | Pauly | F21S 9/022 315/86 |
| 6,170,084 B1 | 1/2001 | Gordon et al. | |
| 6,481,019 B2 * | 11/2002 | Diaz | A41D 13/11 128/201.19 |
| 6,622,311 B2 | 9/2003 | Diaz et al. | |
| 6,752,511 B1 * | 6/2004 | Cramer | A42B 1/242 362/105 |
| 6,792,944 B1 | 9/2004 | Green et al. | |
| 6,918,141 B2 | 7/2005 | Green et al. | |
| 6,928,662 B2 * | 8/2005 | Fournier | A62B 18/00 128/201.24 |
| 6,954,968 B1 * | 10/2005 | Sitbon | H01F 7/0263 2/269 |
| 6,973,677 B2 | 12/2005 | Diaz et al. | |
| 7,093,302 B1 | 8/2006 | Burns | |
| 7,200,873 B2 | 4/2007 | Klotz et al. | |
| 7,225,471 B2 | 6/2007 | Sutter et al. | |
| 7,611,255 B1 * | 11/2009 | Lagassey | F21V 21/0885 362/396 |
| 7,699,485 B1 * | 4/2010 | Lagassey | A41D 1/002 362/105 |
| 7,735,156 B2 | 6/2010 | VanDerWoude et al. | |
| 7,752,682 B2 | 7/2010 | VanDerWoude et al. | |
| 7,937,775 B2 | 5/2011 | Manzella, Jr. et al. | |
| 7,993,046 B2 * | 8/2011 | Wang | G02B 6/001 362/555 |
| 8,147,083 B2 * | 4/2012 | Uke | F21V 14/065 362/249.02 |
| 8,196,224 B2 | 6/2012 | Manzella, Jr. et al. | |
| 8,225,421 B1 | 7/2012 | Froissard | |
| 8,234,722 B2 | 8/2012 | VanDerWoude et al. | |
| 8,261,375 B1 | 9/2012 | Reaux | |
| 8,282,234 B2 | 10/2012 | VanDerWoude et al. | |
| 8,302,599 B2 | 11/2012 | Green | |
| 8,382,314 B2 * | 2/2013 | Ou | F21V 5/043 362/240 |
| 8,407,818 B2 | 4/2013 | VanDerWoude et al. | |
| 8,453,262 B2 | 6/2013 | Green | |
| 8,621,375 B2 | 12/2013 | Berger et al. | |
| 8,621,664 B2 | 1/2014 | Peebles | |
| 8,745,763 B2 | 6/2014 | Cho | |
| 8,819,869 B2 | 9/2014 | VanDerWoude et al. | |
| 8,899,774 B2 | 12/2014 | Strong et al. | |
| 8,955,168 B2 | 2/2015 | Manzella, Jr. et al. | |
| 8,985,791 B1 * | 3/2015 | Hinzmann | F21L 4/027 362/2 |
| 9,050,085 B2 | 6/2015 | Chua | |
| 9,173,437 B2 | 11/2015 | VanDerWoude et al. | |
| 9,400,101 B2 | 7/2016 | Strong et al. | |
| 9,706,808 B2 | 7/2017 | Sclafani et al. | |
| 9,833,032 B2 | 12/2017 | Jacobsen | |
| 9,874,342 B1 * | 1/2018 | Liu | F21V 23/0414 |
| 9,980,529 B1 * | 5/2018 | Hajianpour | F21V 21/0965 |
| 10,069,043 B2 * | 9/2018 | Li | H01L 33/44 |
| 10,253,964 B2 | 4/2019 | Strong et al. | |
| 10,420,386 B1 * | 9/2019 | Jefferis | A42B 3/20 |
| 10,750,800 B2 | 8/2020 | Jefferis et al. | |
| 10,830,428 B2 | 11/2020 | Africa et al. | |
| 11,166,515 B1 * | 11/2021 | Hajianpour | A42B 3/145 |
| 11,268,677 B2 * | 3/2022 | Mei | F21V 14/02 |
| 2001/0024365 A1 * | 9/2001 | Aknine | F21L 4/00 362/285 |
| 2004/0085756 A1 * | 5/2004 | Yu | A42B 3/044 362/105 |
| 2005/0010992 A1 * | 1/2005 | Klotz | A42B 3/225 2/171.3 |
| 2005/0190549 A1 * | 9/2005 | Donaldson | A42B 3/225 362/105 |
| 2006/0213523 A1 * | 9/2006 | VanDerWoude | A41D 13/0025 128/863 |
| 2007/0050898 A1 * | 3/2007 | Larson | A62B 18/045 2/456 |
| 2007/0060011 A1 * | 3/2007 | Daftari | A63H 3/46 446/97 |
| 2009/0038056 A1 * | 2/2009 | Bobbin | A42B 3/044 2/422 |
| 2009/0151054 A1 * | 6/2009 | VanDerWoude | A42B 3/286 2/410 |
| 2011/0004979 A1 * | 1/2011 | VanDerWoude | A42B 3/30 2/422 |
| 2012/0120635 A1 * | 5/2012 | Strong | F21V 29/61 362/373 |
| 2013/0204094 A1 * | 8/2013 | Fiebel | A61B 1/0692 600/249 |
| 2013/0223070 A1 * | 8/2013 | Baker | F21V 21/084 362/244 |
| 2013/0283508 A1 * | 10/2013 | Durham | A42B 3/0406 2/422 |
| 2013/0314904 A1 * | 11/2013 | Dirsa | A42B 3/04 362/108 |
| 2014/0259253 A1 * | 9/2014 | Jacob | A41D 13/1161 2/15 |
| 2015/0073227 A1 * | 3/2015 | Teder | A61B 1/0615 600/249 |
| 2015/0090254 A1 * | 4/2015 | Pavalarajan | A42B 3/286 128/201.23 |
| 2015/0375019 A1 * | 12/2015 | VanDerWoude | A62B 18/003 128/201.29 |
| 2016/0123563 A1 * | 5/2016 | Ferguson | A61B 1/0692 362/277 |
| 2017/0000207 A1 * | 1/2017 | Hajianpour | A42B 3/281 |
| 2017/0215717 A1 * | 8/2017 | Orringer | F21V 33/0068 |
| 2018/0177251 A1 * | 6/2018 | Yoo | A41D 13/1184 |
| 2018/0263326 A1 * | 9/2018 | Ulmer | A42B 3/285 |
| 2018/0368505 A1 * | 12/2018 | Kidman | A42B 3/044 |
| 2019/0111288 A1 * | 4/2019 | Isham | A41D 13/1184 |
| 2019/0231005 A1 * | 8/2019 | Jefferis | A42B 3/225 |
| 2020/0060375 A1 * | 2/2020 | Jascomb | A41D 13/1218 |
| 2020/0109847 A1 * | 4/2020 | Poggio | F21V 21/30 |
| 2020/0208818 A1 * | 7/2020 | Le Bourhis | A42B 1/244 |
| 2020/0275724 A1 * | 9/2020 | Jefferis | A42B 3/286 |
| 2020/0281297 A1 * | 9/2020 | Kaye | F21V 21/096 |
| 2020/0359718 A1 | 11/2020 | Jefferis et al. | |
| 2020/0366872 A1 * | 11/2020 | Vettese | A42B 3/042 |
| 2020/0375272 A1 * | 12/2020 | Ulmer | A41D 13/1218 |
| 2021/0259347 A1 * | 8/2021 | Lambert | A42B 3/044 |
| 2021/0368887 A1 * | 12/2021 | Nguyen | A41D 1/002 |
| 2021/0368904 A1 * | 12/2021 | van Nortwick | A42B 3/283 |
| 2022/0110381 A1 * | 4/2022 | Jefferis | A42B 3/286 |
| 2022/0151321 A1 * | 5/2022 | Hines | A62B 18/04 |

(56) References Cited

U.S. PATENT DOCUMENTS

| | | | |
|---|---|---|---|
| 2022/0273066 A1* | 9/2022 | Isham | A41D 13/1153 |
| 2023/0111620 A1* | 4/2023 | Davie | A42B 3/286 |
| | | | 600/249 |
| 2023/0189904 A1* | 6/2023 | Annen | A61B 3/0083 |
| | | | 24/3.3 |

FOREIGN PATENT DOCUMENTS

| | | | |
|---|---|---|---|
| WO | 0111646 | A2 | 2/2001 |
| WO | 0152675 | A2 | 7/2001 |
| WO | 2007011646 | A2 | 1/2007 |
| WO | 2007011646 | A3 | 4/2007 |
| WO | 2009079292 | A1 | 6/2009 |
| WO | 2017053232 | A1 | 3/2017 |
| WO | 2017112485 | A1 | 6/2017 |
| WO | 2017184479 | A2 | 10/2017 |
| WO | 2017184479 | A8 | 3/2018 |
| WO | 2019147923 | A1 | 8/2019 |

OTHER PUBLICATIONS

Bio-Medical Devices INTL, "MaxAir Systems 2270-01 Pre-Filter DLC Hood Instructions for Use", Available on or before Apr. 2017, 3 pages.

International Search Report for Application No. PCT/US2017/027857 dated Oct. 18, 2017, 2 pages.

International Search Report for Application No. PCT/US2019/015128 dated Jun. 25, 2019, 5 pages.

International Search Report for Application No. PCT/US2019/039523 dated Oct. 15, 2019, 3 pages.

Hanselman, Md., Andrew E. et al., "Contamination Relative to the Activation Timing of Filtered-Exhaust Helmets", J. Arthroplasty, vol. 31, No. 4, Apr. 2016, pp. 776-780.

Non-Final Office Action for U.S. Appl. No. 16/257,668, dated Mar. 18, 2019, 8 pages.

* cited by examiner

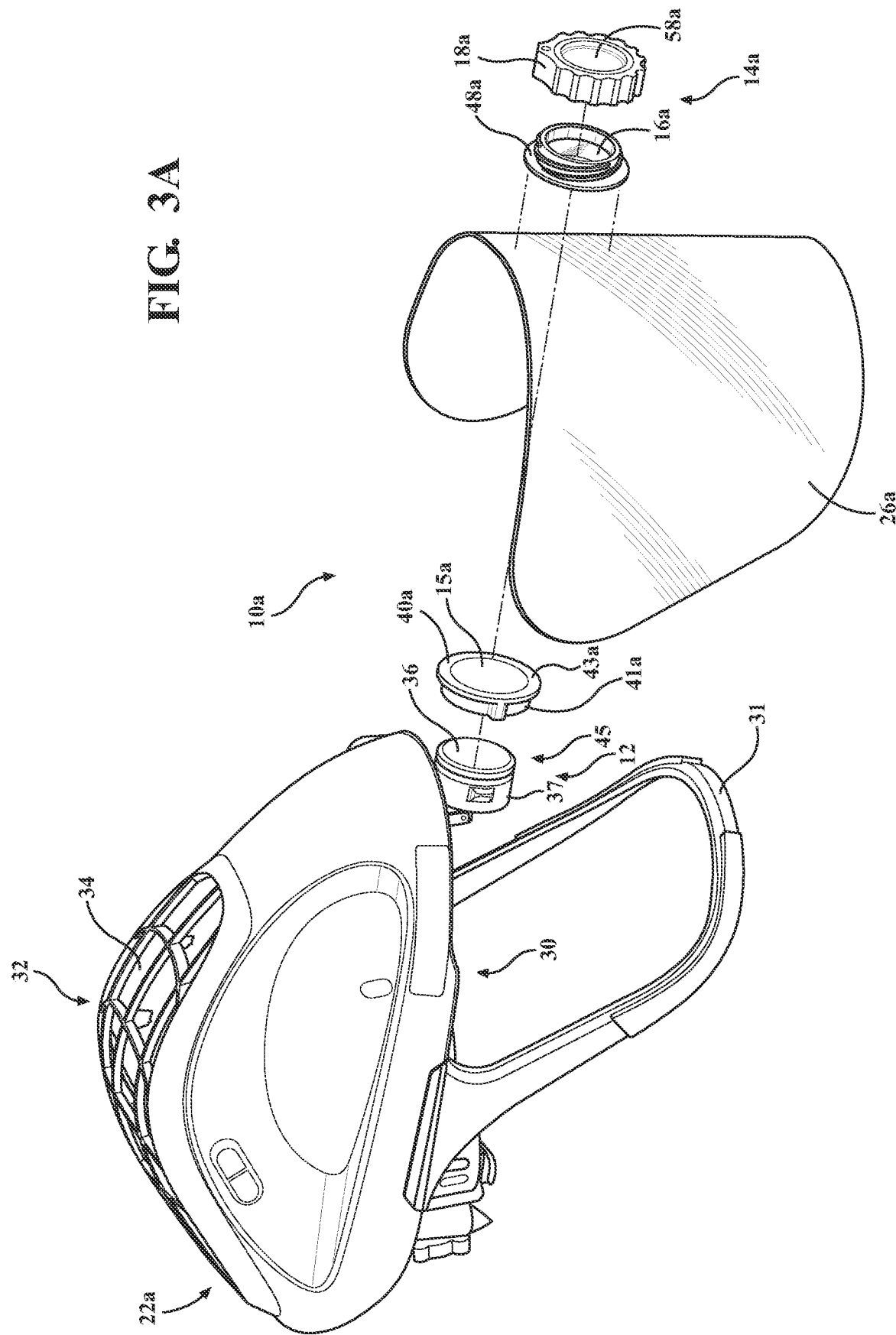

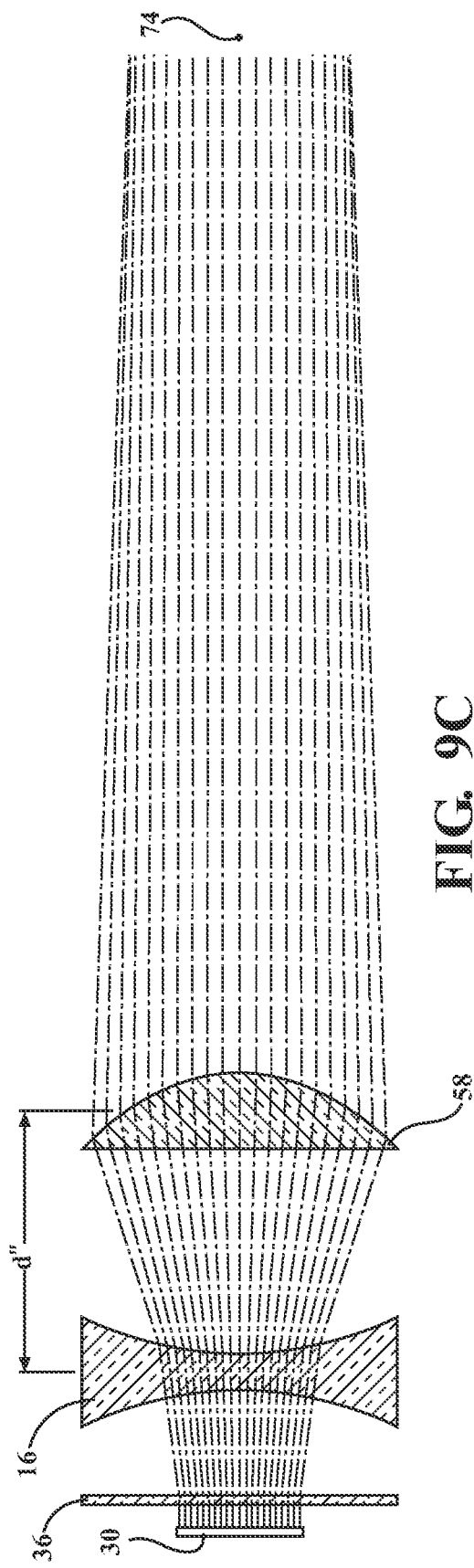
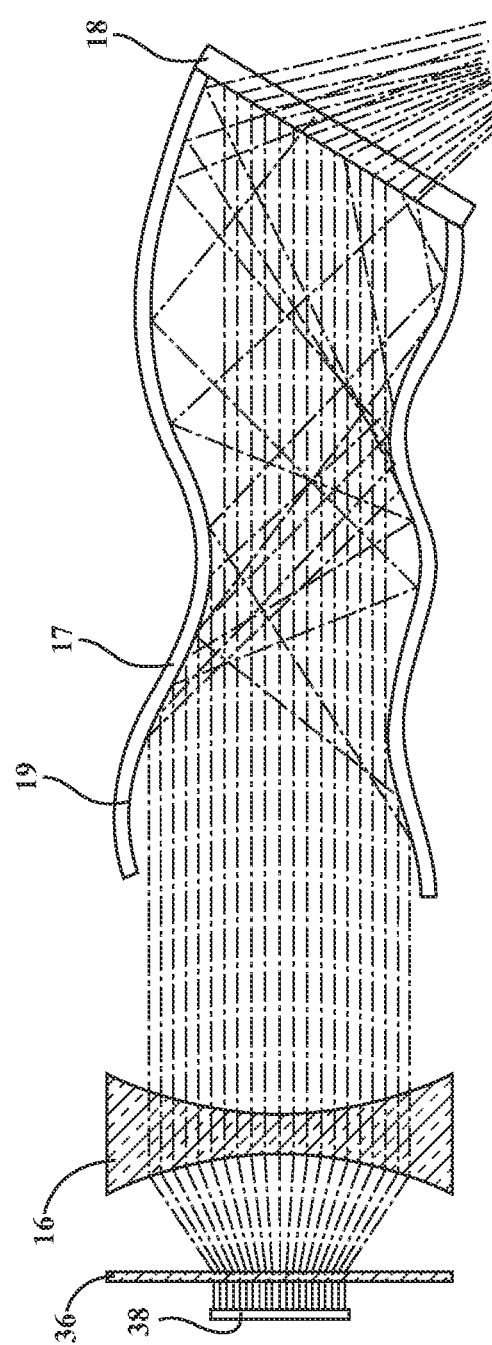

PROTECTIVE APPAREL SYSTEM WITH A LENS ASSEMBLY

RELATED APPLICATIONS

This application claims priority to and the benefit of U.S. Provisional Application No. 62/690,559, filed on Jun. 27, 2018, which is hereby incorporated herein by reference in the entirety.

BACKGROUND

Protective apparel systems are used in surgical procedures to provide a sterile barrier between the medical/surgical personnel and the patient. The protective apparel system includes a helmet that supports a surgical garment. The helmet may include a headlamp to light a portion of a patient or workspace as the medical/surgical personnel operates on the patient. This assemblage is worn by medical/surgical personnel to establish the sterile barrier.

The sterile barrier prevents the exchange and/or transfer of particles or foreign material during the surgical procedure or examination. In addition, the barrier serves to protect the wearer from exposure to blood and other bodily fluids. Maintaining a reliable barrier between the wearer and the patient is of the utmost importance.

During medical and surgical procedures, a wearer may need to adjust or redirect the light from the headlamp for better visibility and lighting of the workspace. Adjustments or redirections of the light from the headlamp require adjustment, tilt, or manipulation of the headlamp. For example, the headlamp may be tilted downwards to illuminate the patient's body. Currently, the wearer adjusts the headlamp through the surgical garment. At the same time, maintaining visibility of the surgical workspace is paramount. By tilting the headlamp downwards, the visibility of the workspace is decreased. Thus, any adjustment of the headlamp during the procedure should not compromise visibility of the procedure.

Furthermore, there may be instances where the headlamp position, while preoperatively acceptable, becomes unacceptable during the procedure. In such instances, the procedure may be delayed until proper adjustment of the headlamp is obtained. This decreases the efficiency of the procedure by delaying the procedure.

A protective apparel system with features designed to overcome at least the aforementioned challenges is desired. These and other configurations, features, and advantages of the present disclosure will be apparent to those skilled in the art. The present disclosure is not to be limited to or by these configurations, features, and advantages.

BRIEF SUMMARY

One configuration of a wearable surgical garment is provided for use with a surgical helmet having a headlamp. The surgical garment comprises a surgical fabric configured to provide a microbial barrier between a medical environment and a wearer. The surgical garment defines an environment side and a wearer side. A coupling member is provided on the wearer side. A lens assembly is coupled to the surgical fabric on the environment side. The coupling member may function to couple to the headlamp on the wearer side such that the headlamp is aligned to the lens assembly. The lens assembly aligns with the headlamp such that the light emitted by the headlamp is transmitted through the lens assembly. The lens assembly comprises a first lens and a control member wherein the control member is operatively coupled to the first lens. The control member is manipulatable by the wearer on the environment side of the surgical garment to adjust a characteristic of the lens assembly.

One configuration of a protective apparel apparatus is provided for use with a surgical helmet having a headlamp. The protective apparel apparatus comprises a wearable surgical garment and a lens assembly. The wearable surgical garment defines an environment side and a wearer side. The surgical garment comprises a surgical fabric configured to provide a microbial barrier between a medical environment and a wearer. The lens assembly is coupled to the surgical garment on the environment side and configured to be aligned with the headlamp. The lens assembly comprises a housing, a first lens coupled to the housing, and a control member coupled to the housing. The control member is operatively coupled to the first lens. The control member is manipulatable by the wearer on the environment side of the surgical garment to adjust a characteristic of the lens assembly.

One configuration of a protective apparel system is provided. A protective apparel system comprises a surgical helmet to be worn over the head of a wearer. The surgical helmet comprises a headlamp. The protective apparel system comprises a surgical garment configured to be at least partially disposed over the surgical helmet. The surgical garment defines an environment side and a wearer side. The surgical garment comprises a surgical fabric configured to provide a microbial barrier between a medical environment and a wearer. A coupling member is provided on the wearer side. The surgical garment further comprises a lens assembly coupled to the surgical garment on the environment side. The lens assembly is configured to be aligned with the headlamp such that the light emitted by the headlamp is transmitted through the lens assembly. The lens assembly comprises a housing, a first lens coupled to the housing, a control member coupled to the housing, and a second lens. The control member is operatively coupled to the second lens and manipulatable by the wearer on the environment side of the surgical garment to adjust a characteristic of the lens assembly. The manipulation of the control member by the wearer on the environment side of the surgical garment adjusts the position of the second lens relative to the first lens to direct the light emitted from the headlamp without breaching the sterile barrier.

The surgical garment, protective apparel apparatus, and the protective apparel system provide solutions to problems that have not been addressed by prior techniques. The techniques described herein provide a solution for adjusting the light from a headlamp without breaching the sterile barrier, which maintains the sterility of the procedure. Thus, the surgical garment, protective apparel apparatus and the protective apparel system provide a solution to optimally satisfy this delicate balance involved with headlamp adjustments and maintaining a sterile barrier. Moreover, any detrimental consequences on the procedure resulting are mitigated because the techniques ensure proper adjustment of the light from the headlamp as well as maintaining the sterile barrier during a procedure. Accordingly, the techniques herein provide a solution to adjustment of light from a headlamp thereby increasing probability of a successful surgical procedure and eliminating breaching of the sterile barrier during the surgical procedure.

The surgical garment, protective apparel apparatus and the protective apparel system may provide solutions other than those described above.

BRIEF DESCRIPTION OF THE DRAWINGS

Referring now to the drawings, exemplary illustrations are shown in detail. Although the drawings represent schematic configurations, the drawings are not necessarily to scale and certain features may be exaggerated to better illustrate and explain an innovative aspect of an illustrative configuration. Further, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings.

FIG. 3A is a partially exploded view of an exemplary configuration of the protective apparel system of FIG. 1A including a surgical helmet with a headlamp and a first configuration of a lens assembly for use with the face shield of the first configuration of the surgical garment of FIG. 2A.

FIG. 9C is a schematic view of FIG. 8C illustrating an exemplary light pattern produced by the second configuration of the lens assembly including a first lens and a second lens when the control member is positioned at the third distance away from the housing.

FIG. 10 is a schematic view of an exemplary light pattern produced by the third configuration of the light assembly of FIG. 3C.

DETAILED DESCRIPTION

I. Overview of Patient Apparel System

Maintaining a sterile barrier between a medical personnel/healthcare provider and a patient to prevent the exchange and/or transfer of particles or foreign material during a medical procedure or examination is of the utmost importance. The healthcare provider may wear an assembly known as a protective apparel system 5 to maintain the sterile barrier.

Figure 1A:
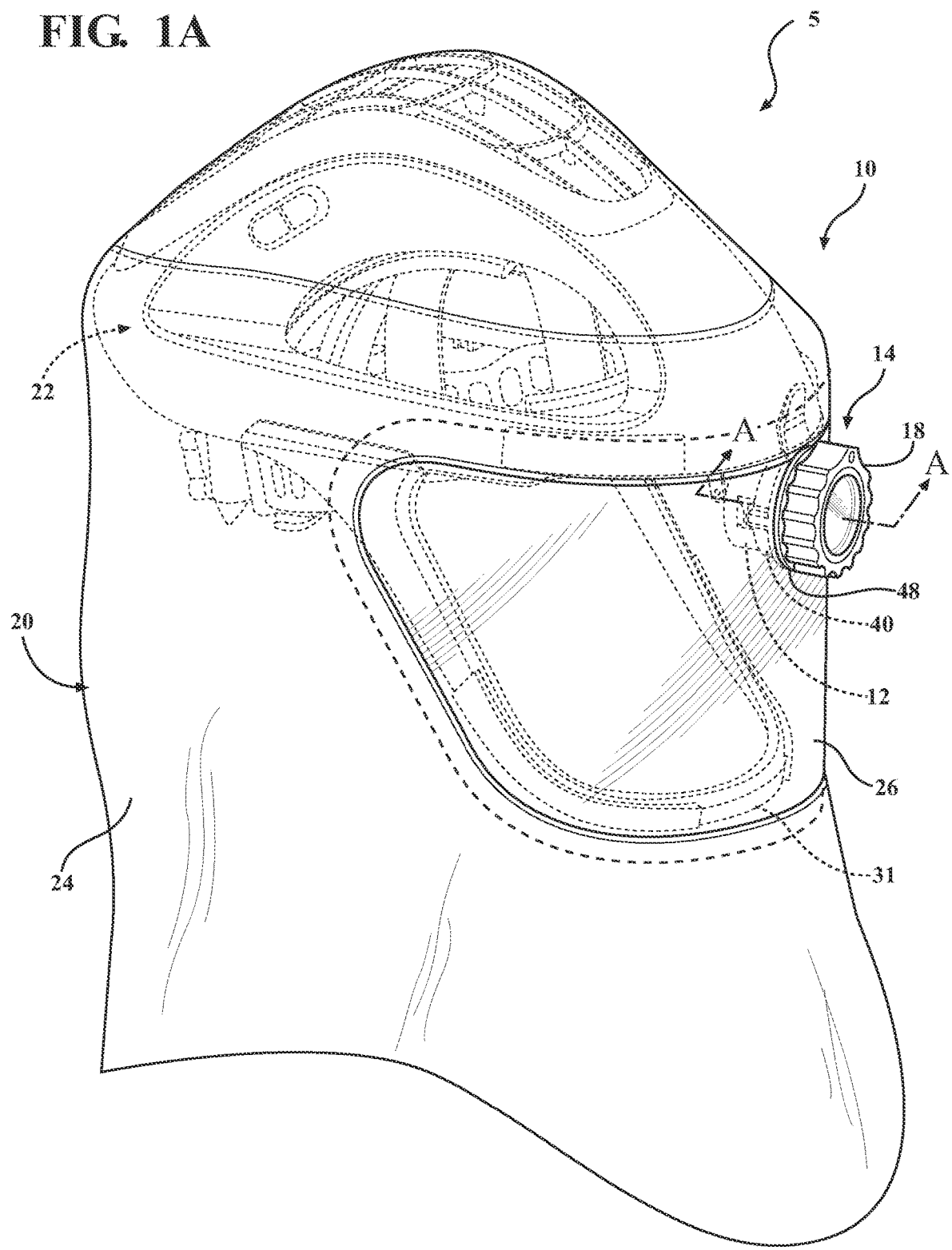
FIG. 1A is a perspective view of an exemplary configuration of a protective apparel system that includes a surgical helmet, a surgical garment, and a lens assembly, with the surgical helmet shown in phantom.

Referring to FIG. 1A, an exemplary configuration of a protective apparel system 5, including a protective apparel apparatus 10 and a surgical helmet 22, is illustrated. Accordingly, the protective apparel apparatus 10 may comprise a wearable surgical garment 20 configured to be at least partially disposed over the surgical helmet 22, as shown in FIG. 1A. The surgical garment 20 may include a surgical fabric 24 configured to cover the surgical helmet 22 and at least a portion of the head of the wearer. The protective apparel apparatus 10 may also comprise a shield 26 coupled to the surgical garment 20. The protective apparel apparatus 10 may also comprise a lens assembly 14 that may be coupled to the surgical garment 20 or the shield 26. Collectively, the features of the protective apparel apparatus 10 may be configured to define a sterile barrier between the wearer side and the environment side of the protective apparel apparatus 10. Additional features and variations of the protective apparel apparatus 10 that may form a part of the protective apparel system 5 will be described in greater detail below.

Figure 1B:
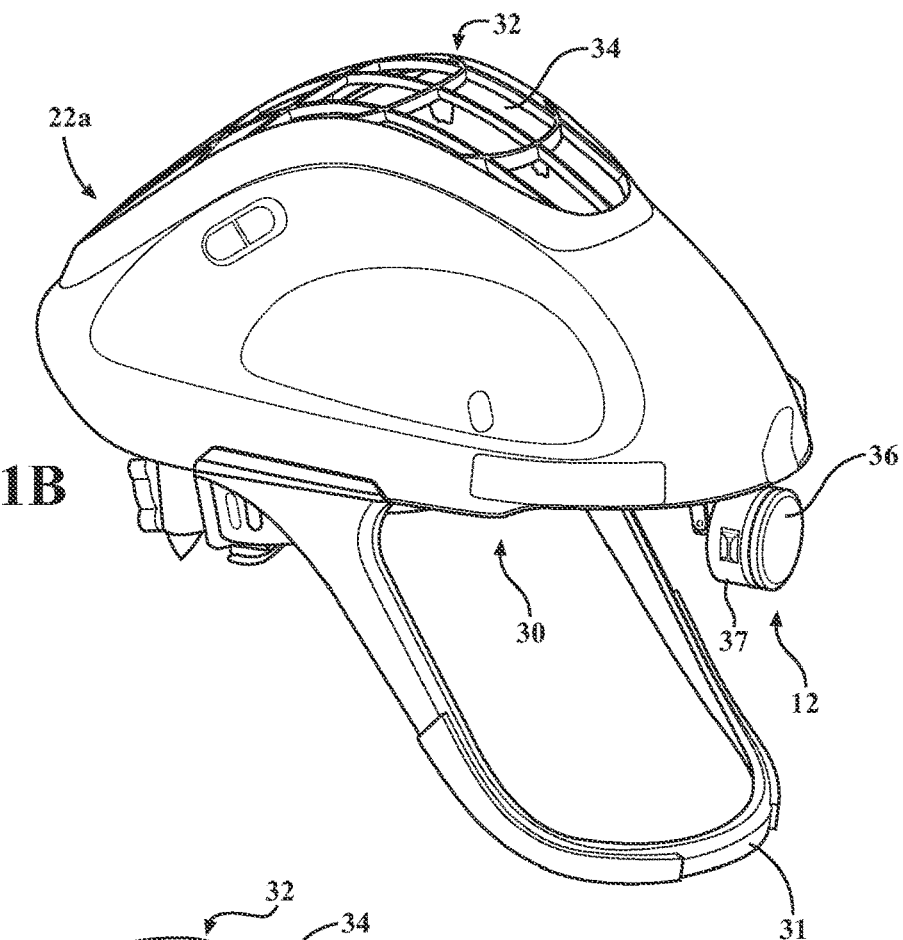
FIG. 1B is a perspective view of a first configuration of the surgical helmet of the protective apparel system of FIG. 1A, the surgical helmet including a headlamp.
Figure 1C:
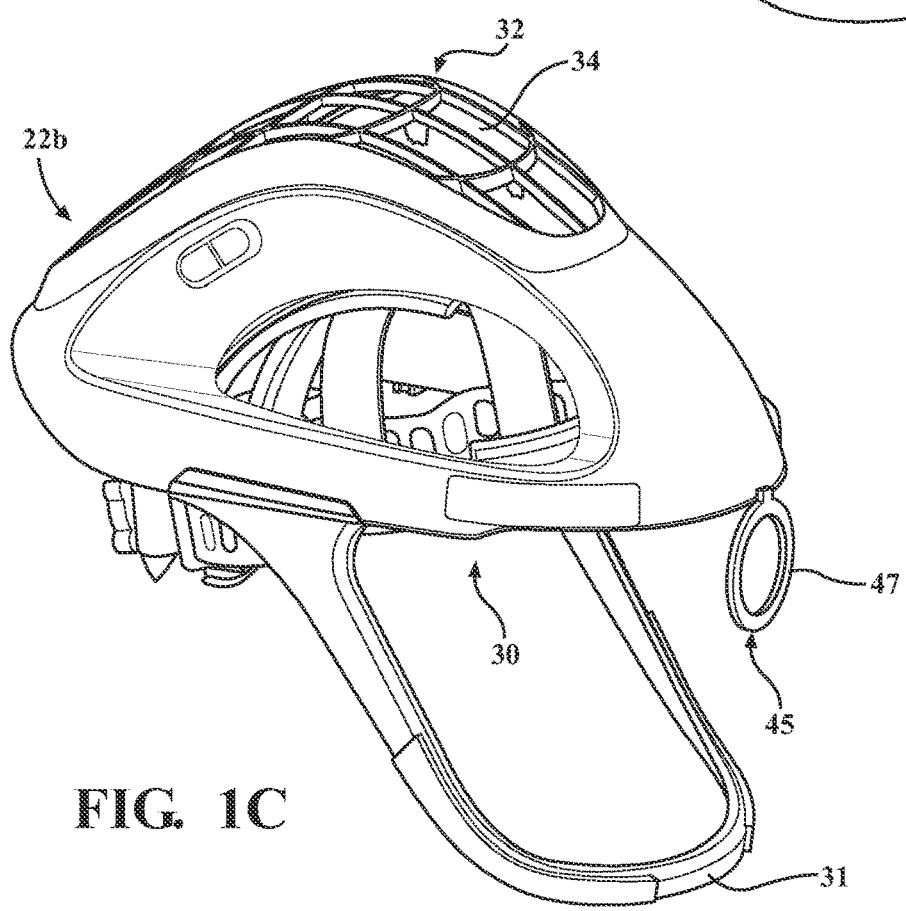
FIG. 1C is a perspective view of a second configuration of the surgical helmet of the protective apparel system of FIG. 1A, the surgical helmet including a headlamp.

The protective apparel system 5 may include the surgical helmet 22. Referring to FIGS. 1B and 1C, exemplary configurations of the surgical helmet 22 that may be used with the protective apparel apparatus 10 as part of the protective apparel system 5 are illustrated. Each configuration of the surgical helmet 22 may generally include a shell 32, a chin bar 31, and a headband 30. The shell 32 is supported by and located above the headband 30. The shell 32 may be configured in an arcuate shape to fit over the head of the wearer. Other helmet designs are contemplated. Many portions of the shell 32 may be formed to define voids, or open interior spaces. For example, the shell 32 may comprise a center void 34. The center void 34 may be located towards the rear of the shell 32. There may be an intake opening or aperture in the top portion of the shell 32 to provide access to the center void 34. The shell 32 may also include additional voids, such as a front void proximate to the front of the shell 32 and a rear void proximate to the rear of the shell 32. The additional voids may be configured to form duct-like structures or passageways within the shell 32.

The surgical helmet 22 may also include one or more peripheral devices, including, but not limited to, a ventilation assembly, a headlamp 12, a camera, a microphone or other communication device, a cooling device, or combinations thereof. For example, a ventilation assembly may be positioned within the shell 32 of the surgical helmet 22 above the head of a wearer. The ventilation assembly may be configured to draw air into the center void 34 of the shell 32 and disperse it through the duct-like structures or passageways within the shell 32. It is contemplated that the peripheral device may also include a microphone disposed in the chin bar 31. In yet another example, the peripheral device may also include a headlamp 12. The headlamp 12 may be coupled to the shell 32 of the surgical helmet 22. While example configurations of the surgical helmet 22 including a peripheral device are described above, the examples are not intended to be limiting. It is contemplated that the peripheral devices described above may be mounted to and/or attached at various locations and orientations relative to the surgical helmet 22.

Additional features of the protective apparel apparatus 10, the surgical helmet 22 and the peripheral devices may be described in one or more of the following U.S. Patents, which are hereby incorporated by reference: U.S. Pat. Nos. 6,481,019; 7,752,682; 9,706,808; 6,973,677; 7,735,156; 7,752,682; 8,234,722; 8,282,234; 8,407,818; 8,819,869; and 9,173,437.

Referring to FIGS. 1B and 1C, exemplary configurations of the surgical helmet 22 for use with a peripheral device, such as a headlamp 12, are illustrated. The headlamp 12 may couple to the surgical helmet 22 in any suitable manner. For example, in one configuration, the headlamp 12 may be integrally formed with the helmet 22. In another configuration, the headlamp 12 may be removably coupled to the helmet 22. In yet another configuration, the headlamp 12 may couple to the helmet 22 via a fastener. The fastener may include a bolt, screw, pin, hinge, bracket, or the like to couple the headlamp 12 to the helmet 22.

The headlamp 12 may include a headlamp body 37. The headlamp body 37 may be formed in any suitable configuration. The headlamp 12 may also comprise a transparent cover 36 and a light source 38 (not shown in FIG. 1B) at least partially disposed within the headlamp body 37. The transparent cover 36 may comprise a lens, screen, shield, or other similar cover mechanism configured to allow light to pass through. The transparent cover 36 may be configured to cover a headlamp opening defined by the headlamp body 37 in order to prevent dust, dirt, or moisture from entering the inside of the headlamp 12, while also allowing light transmitted by the light source 38 to pass through. The light source 38 may comprise one or more light emitting diodes (LEDs). The number and type of light emitting diodes may be determined by the desired beam intensity, beam width, electrical power requirement, heat generation and space availability. Other light sources 38 are also contemplated, such as incandescent filaments and the like. Moreover, depending on the required luminous efficacy and required light colors, the light emitting diodes emitting isochromatic or heterochromatic light may be used as the light source 38. In other configurations, the light source 38 may be from any method of generation of light, such as incandescent, luminescent, combustion, fiber optic, and the like.

In one configuration, the headlamp 12 and/or the light source 38 may be battery powered with an internal battery. In another configuration, the headlamp 12 and/or the light source 38 may be coupled to a controller or an external power supply by leads. For example, the headlamp 12 and/or the light source 38 may be self-powered with an internal power supply or may receive power through a host object, if available.

Referring to FIG. 1B, a first exemplary configuration of the surgical helmet 22A is illustrated. The surgical helmet 22A may include the headlamp 12 coupled directly to the shell 32 of the helmet 22A to assist with illuminating or lighting the surgical workspace. The headlamp 12 may be coupled to the shell 32 of the surgical helmet 22A by a hinge, pin, screw, pivot, bracket, hook and loop, or the like. For example, the headlamp 12 may include a bracket configured to engage a corresponding bracket on the shell 32 of the surgical helmet 22. The corresponding brackets of the shell 32 and the headlamp 12 may be coupled by a screw, pin, or the like, and configured to allow the headlamp 12 to be pivoted relative to the shell 32. Alternatively, the headlamp 12 may comprise a bracket including a ball and the shell 32 may comprise a corresponding cavity or recess configured to form a press fit with the ball of the headlamp 12. It is further contemplated that the headlamp 12 may comprise a bracket that is coupled directly to the shell 32 of the surgical helmet 22 by a screw, bolt, or similar fastener. In this configuration of the headlamp 12, the bracket may comprise a pivot, hinge, or similar mechanism to allow the headlamp 12 to be manipulated relative to the surgical helmet 22 when coupled to the shell 32. While FIG. 1B generally illustrates the headlamp 12 being coupled to the underside of the shell 32 on the front of the surgical helmet 22A, it is contemplated that the headlamp 12 may be coupled at other locations on the surgical helmet 22A. For example, it is also contemplated that the headlamp 12 may be coupled to the headband 30 of the surgical helmet 22A in a similar manner.

Alternatively, it is also contemplated that the headlamp 12 may be removably coupled to the surgical helmet 22B by a separate mounting feature 45. FIG. 1C illustrates a second exemplary configuration of the surgical helmet 22B including a mounting feature 45, such as a bracket, for coupling a peripheral device, such as the headlamp 12, to the surgical helmet 22B. For example, as illustrated in FIG. 1C, the mounting feature 45 may be coupled to the shell 32 of the surgical helmet 22. The mounting feature 45 may be coupled to the shell 32 by a screw, bolt, pin, adhesive, hook and loop, or other similar fastener. For example, the mounting feature 45 may be adhered to the shell 32 using an epoxy or similar adhesive. Alternatively, the mounting feature 45 may be coupled to the shell 32 using one or more screws.

The mounting feature 45 may also comprise an attachment portion 47 configured to receive the peripheral device, such as the headlamp 12. For example, as illustrated in FIG. 1C, the bracket includes a ring-shaped attachment portion 47 configured to receive and/or couple to the headlamp 12. While the exemplary configuration of the attachment portion 47 is illustrated as being ring-shaped in FIG. 1C, other shapes are contemplated. For example, the attachment portion 47 may be configured in a U-shape, square, or other similar shape. The attachment portion 47 may be sized and/or shaped to create a friction fit with the peripheral device, such as the headlamp 12. Alternatively, it is contemplated that the attachment portion 47 may comprise a coupling feature that engages a corresponding feature of the headlamp 12. For example, the attachment portion 47 may comprise a threaded portion, such as on the interior of the aperture defined by the ring-shape, that is configured to engage a corresponding threaded portion on the exterior of the headlamp 12. Alternatively, the attachment portion 47 may comprise one or more grooves cut in the interior of the aperture defined by the ring-shape that are configured to engage corresponding tabs and/or protrusions on the exterior of the headlamp 12 to couple the headlamp 12 to the attachment portion 47. In yet another configuration, it is contemplated that the attachment portion 47 may comprise one or more apertures for receiving a fastener such as a pin bolt, or screw, such that the headlamp 12 may be fastened to the attachment portion 47.

It is also contemplated that the attachment portion 47 of the mounting feature 45 may be configured to couple to and/or engage the protective apparel apparatus 10. For example, the attachment portion 47 may be configured to removably engage the face shield 26 of the protective apparel apparatus 10 to orient the protective apparel apparatus 10 and/or the face shield 26 relative to the surgical helmet 22B. This may include aligning the protective apparel apparatus 10 and/or the face shield 26 with the peripheral device, such as the headlamp 12, that is attached to the mounting feature 45.

The mounting feature 45 may further comprise a hinge, pivot, or similar mechanism configured to allow the attachment portion 47 of the mounting feature 45 to be manipulated relative to the shell 32 and or surgical helmet 22B. For example, the mounting feature 45 may comprise a hinge that allows the attachment portion 47 to be folded/swung out of the way when not needed. This would allow the attachment portion 47 to be moved out of the wearer's field of view when not needed, removing a potential obstruction or distraction from the wearer's field of view during a surgical procedure.

As described above, the protective apparel system 5 may comprise a protective apparel apparatus 10 configured to be at least partially disposed over the surgical helmet 22A, 22B when worn by a medical professional. During the procedure, it may be necessary to the headlamp 12 that is coupled to the surgical helmet 22A, 22B and is on the wearer side of the barrier defined by the protective apparel apparatus 10. However, it would be disadvantageous if the medical professional were required to adjust the headlamp 12 during the medical procedure without compromising the sterile barrier. Therefore, a protective apparel apparatus 10 including a lens assembly 14 that is at least partially disposed on the environment side of the sterile barrier defined by the protective apparel apparatus 10 and allows for adjustment of the intensity and/or direction of the light emitted from the headlamp 12 without breaking the sterile barrier defined by the protective apparatus 10 is disclosed.

Figure 2A:
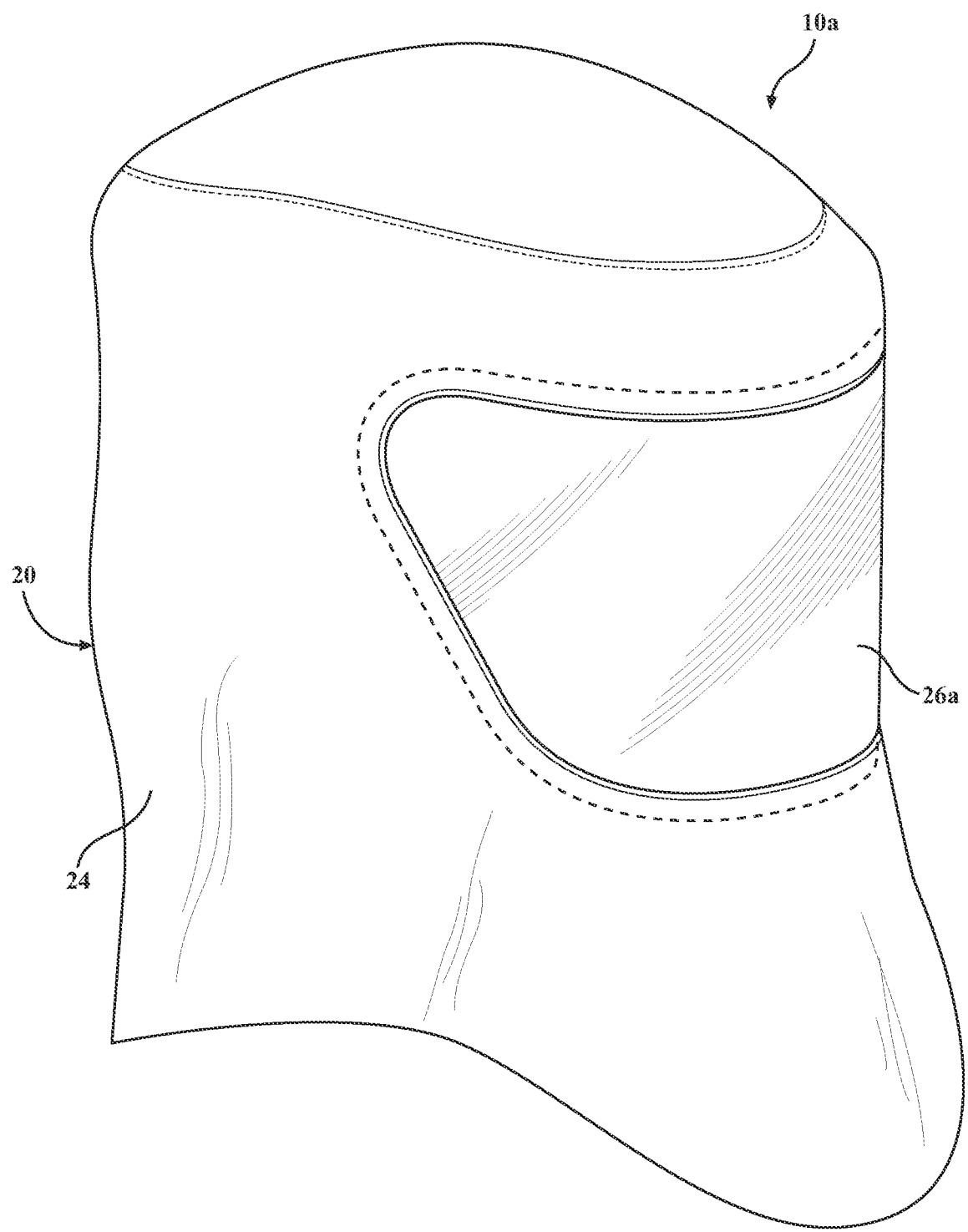
FIG. 2A is a perspective view of a first configuration of a surgical garment of the protective apparel system of FIG. 1A.
Figure 2B:
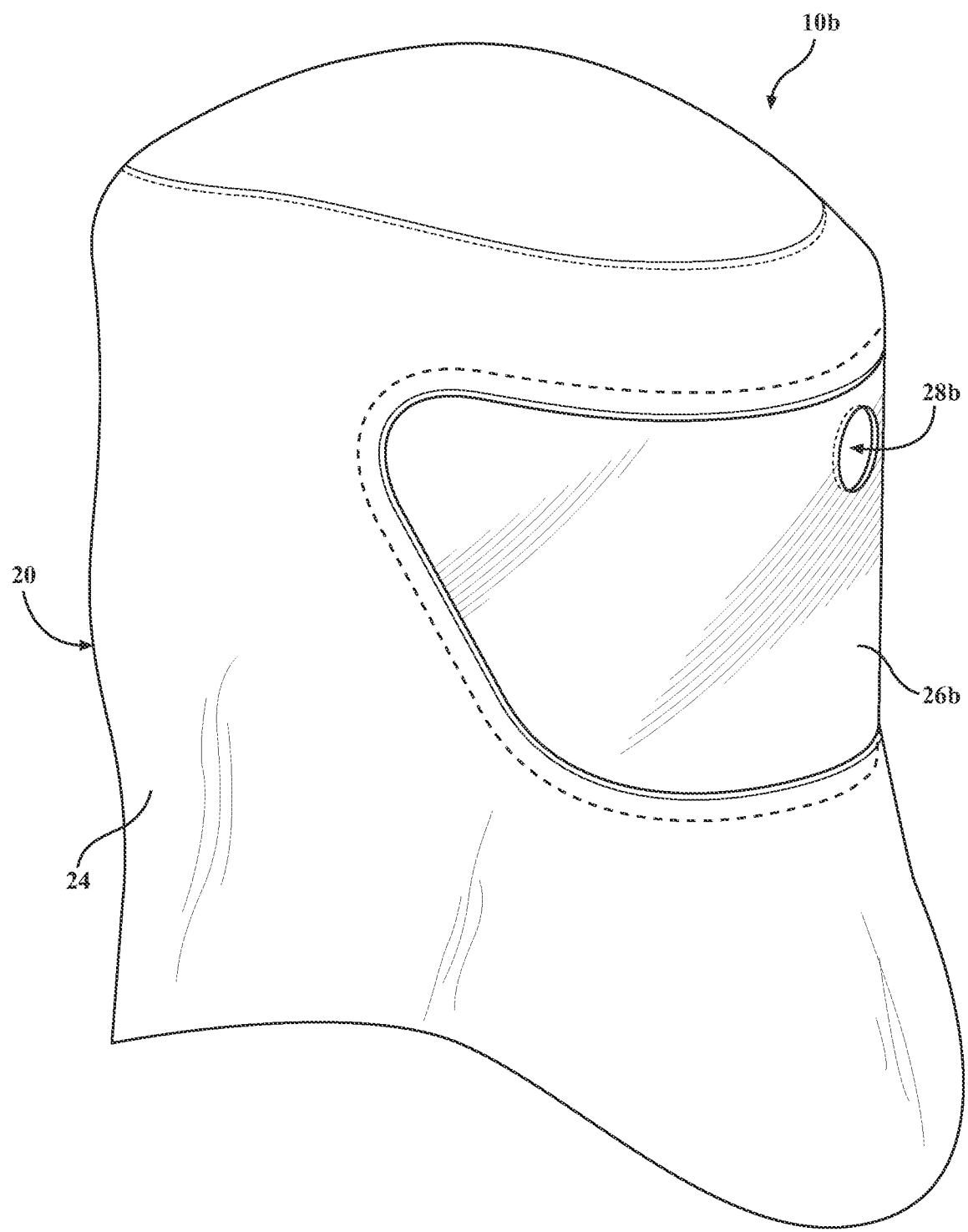
FIG. 2B is a perspective view of a second configuration of a surgical garment of the protective apparel system of FIG. 1A, the face shield of the surgical garment including an opening.
Figure 2C:
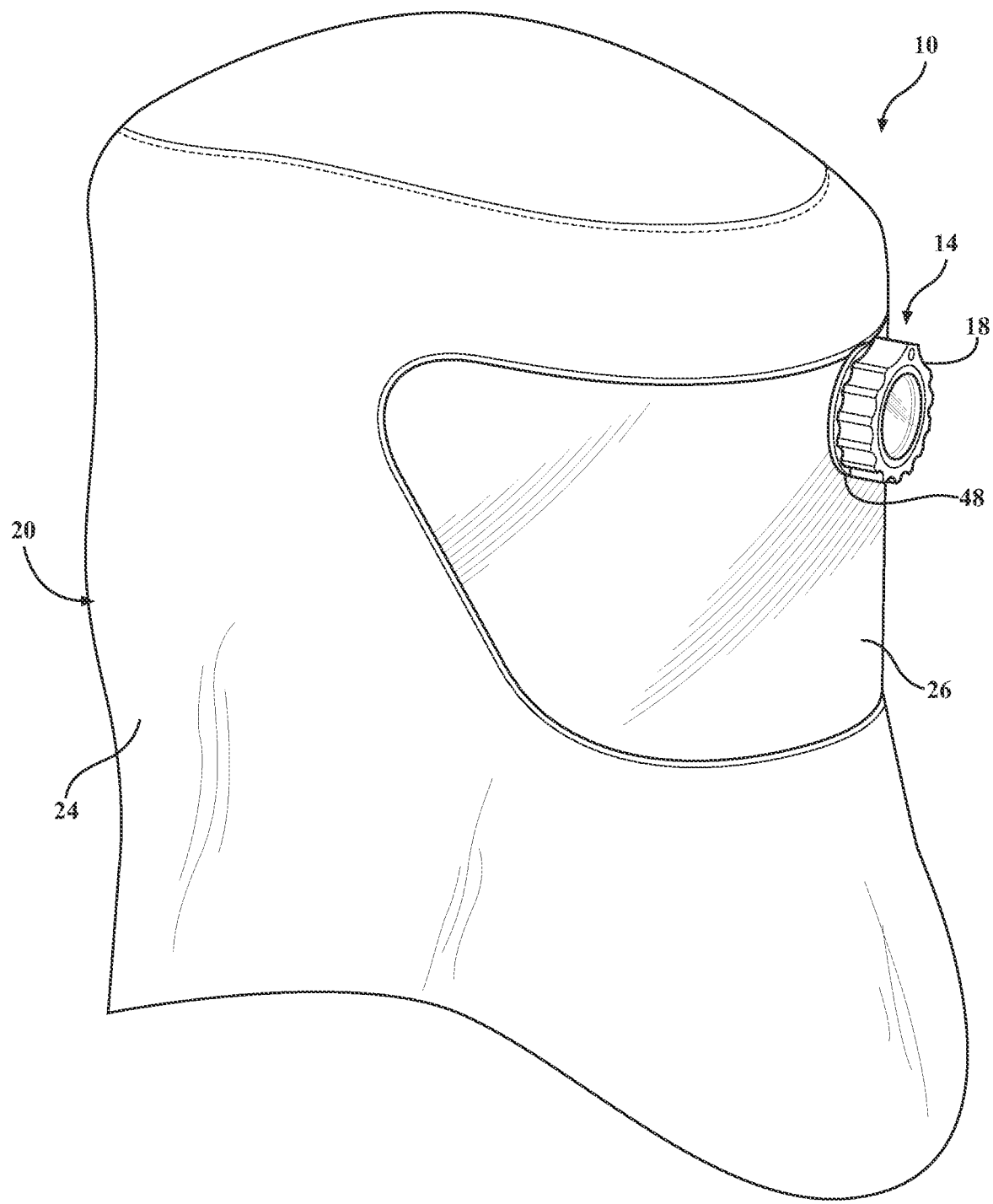
FIG. 2C is a perspective view of a third configuration of a surgical garment of the protective apparel system of FIG. 1A, the surgical garment including a lens assembly comprising a housing and a control member.

Referring to FIGS. 2A-2C, various exemplary configurations of the protective apparel apparatus 10A, 10B, 10C for use with the protective apparel system 5 of FIG. 1A are illustrated. It will be understood that the protective apparel apparatus 10A, 10B, 10C may be configured to define an environment side and a wearer side. The barrier may substantially eliminate the likelihood that the wearer may be exposed to the fluid or solid particles of matter from the patient that may be generated during the course of a surgical procedure. The barrier may substantially prevent the transfer of any foreign particles emitted by the wearer from being transferred to the patient during the surgical procedure. The protective apparel apparatus 10 may comprise a surgical garment 20 comprises a surgical fabric 24 configured to at least partially define a barrier, such as a microbial barrier, between the wearer and the surrounding environment. The surgical garment 20 may be configured as a hood or a toga to be placed over the surgical helmet 22A, 22B. In one configuration, as shown in FIGS. 1 and 2A, the surgical garment 20 may be a hood. A hood refers to a surgical garment 20 that covers the head and likely only extends a short distance below the neck when worn by the wearer. Moreover, the surgical garment 20 may be positioned over the surgical helmet 22 and configured to encompass the surgical helmet 22A, 22B and, correspondingly, the head of the person wearing the system 5, thereby covering the wearer's face and back of the head. Alternatively, the surgical garment 20 may be a toga, a shirt, or a jacket. In another instance, the toga refers to the surgical garment 20 that covers the head in the same manner as a hood and extends to at least the waist when worn by the wearer.

The surgical garment 20 may be manufactured from any suitable surgical fabric 24 or combinations of fabrics to help repel and/or absorb water, debris, and other contaminants. The surgical fabric 24 may include multiple layers. One such layer may be a microporous film that allows gas to pass through the fabric 24 while maintaining the microbial barrier. It is further contemplated that the surgical garment 20 may be constructed of multiple different fabrics coupled to one another to define the barrier.

The protective apparel apparatus 10 may also comprise a face shield 26A, 26B. The face shield 26A, 26B portion of the protective apparel apparatus 10A, 10B, 10C enables the wearer to see through the barrier provided by the surgical garment 20. The face shield 26A, 26B is generally a sheet-like structure and may have any suitable thickness. The face shield 26 may be mounted and/or attached to an opening or cutout formed in the fabric 24 of the surgical garment 20. The fabric 24 may be attached around the periphery or edge of the face shield 26A, 26B by sewing, snaps, hook and hoop, adhesive, welding, or any combinations thereof. The face shield 26A, 26B may be constructed from a transparent material, such as a polycarbonate. The face shield 26A, 26B may also be tinted to protect the wearer's eyes from heightened exposure of bright lights. Furthermore, the face shield 26A, 26B may be flexible such that the face shield 26 may be curved to accommodate different head sizes. The face shield 26A, 26B will be positioned in front of the wearer's face when the surgical garment 20 is disposed over a surgical helmet worn by a medical professional.

Referring to FIG. 2A, a first configuration of protective apparel apparatus 10A including a first configuration of a face shield 26A is illustrated. In this configuration of the protective apparel apparatus 10A, the face shield 26A comprises a sheet-like structure that is disposed in an opening in the surgical garment 20. The opening of the surgical garment 20 couples to the periphery of the shield 26A such that any holes or apertures in the shield 26A are covered by the surgical garment 20, creating a solid sterile barrier between the wearer and the environment. This may include the surgical garment 20 covering an opening in the top of the face shield 26A that is configured to couple with the surgical helmet 22A, 22B. The surgical garment 20 may also cover ferrous or magnetic rivets that are coupled to the face shield 26A configured to couple with a corresponding fastener on the surgical helmet 22A, 22B.

Referring to FIG. 2B, a second configuration of protective apparel apparatus 10B including a second configuration of a face shield 26B is illustrated. The face shield 26B may comprise one or more openings 28. For example, the face shield 26B, as illustrated in FIG. 2B, may comprise one opening 28. The opening may be configured to interact with and/or engage the headlamp 12 of the surgical helmet 22 and/or the lens assembly 14. Alternatively, it is also contemplated that the face shield 26B may comprise two openings. For example, the face shield 26B comprises a first opening 28 for use with the headlamp 12 and/or the lens assembly 14 and a second opening for securing the surgical helmet 22A, 22B to the face shield 26B. In this instance, the protective apparel apparatus 10B may be disposed over the helmet 22A, 22B as illustrated in FIG. 1A. In one configuration, the surgical helmet 22A, 22B may comprise a tab configured to mate with the second opening or aperture in the face shield 26B. However, the second opening in the face shield 26B would be covered by the surgical garment, so as not to be exposed.

Referring to FIG. 2C, an exemplary configuration of a protective apparel apparatus 10A including a lens assembly 14A coupled to the face shield 26A. The lens assembly 14 may be coupled to the protective apparel apparatus 10 such that it is manipulatable by the wearer, on the environment side, to direct and/or manipulate the intensity and/or direction of the light from the headlamp without having to break the sterile barrier. The lens assembly 14 may be manipulated to adjust, tilt, focus, and/or manipulate the headlamp itself in order to direct the light to the surgical workspace. The lens assembly 14 will be described in detail further below.

Figure 3B:
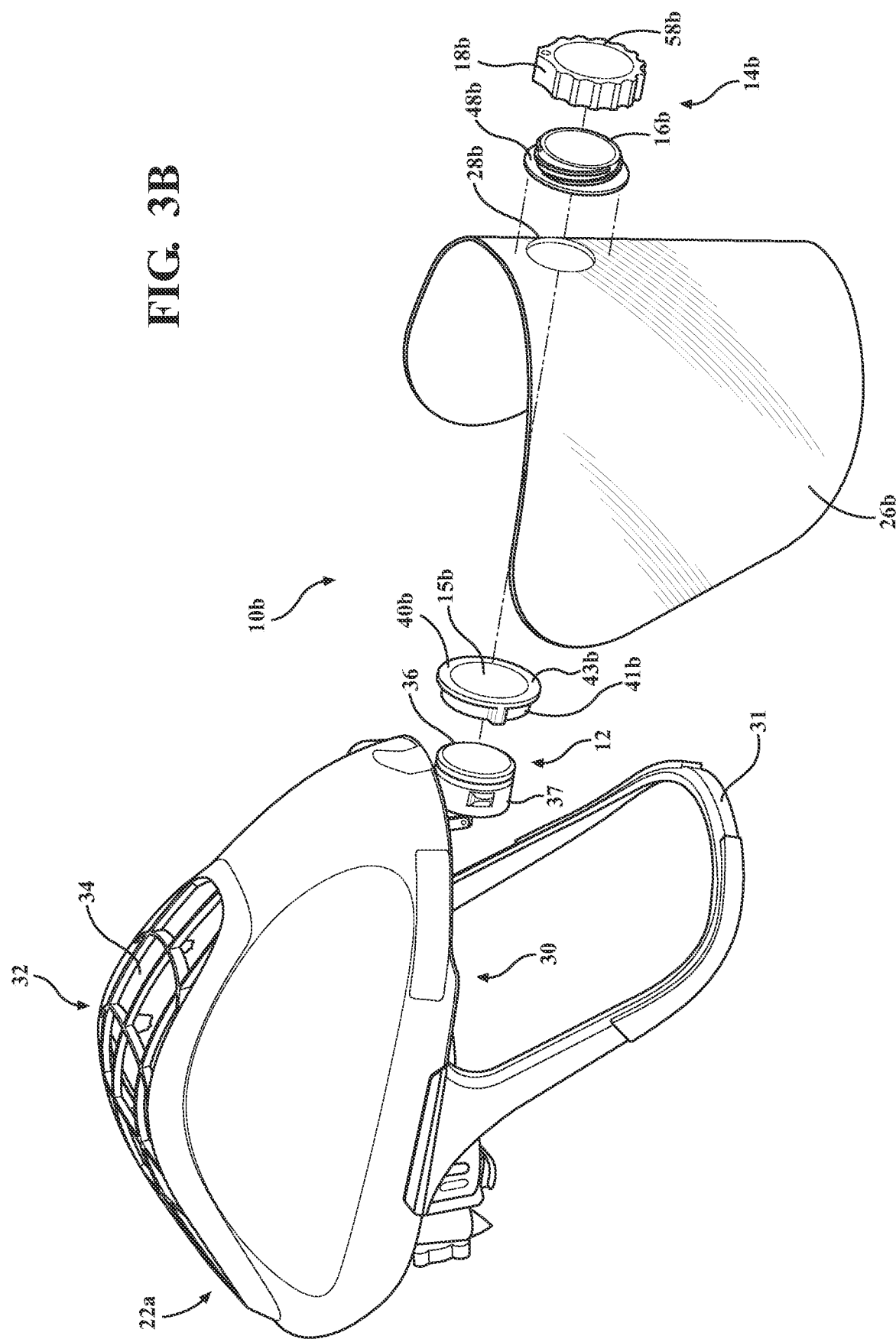
FIG. 3B is a partially exploded view of an exemplary configuration of the protective apparel system of FIG. 1A including a surgical helmet with a headlamp and a second configuration of a lens assembly for use with the face shield of the second configuration of the surgical garment of FIG. 2B.
Figure 3C:
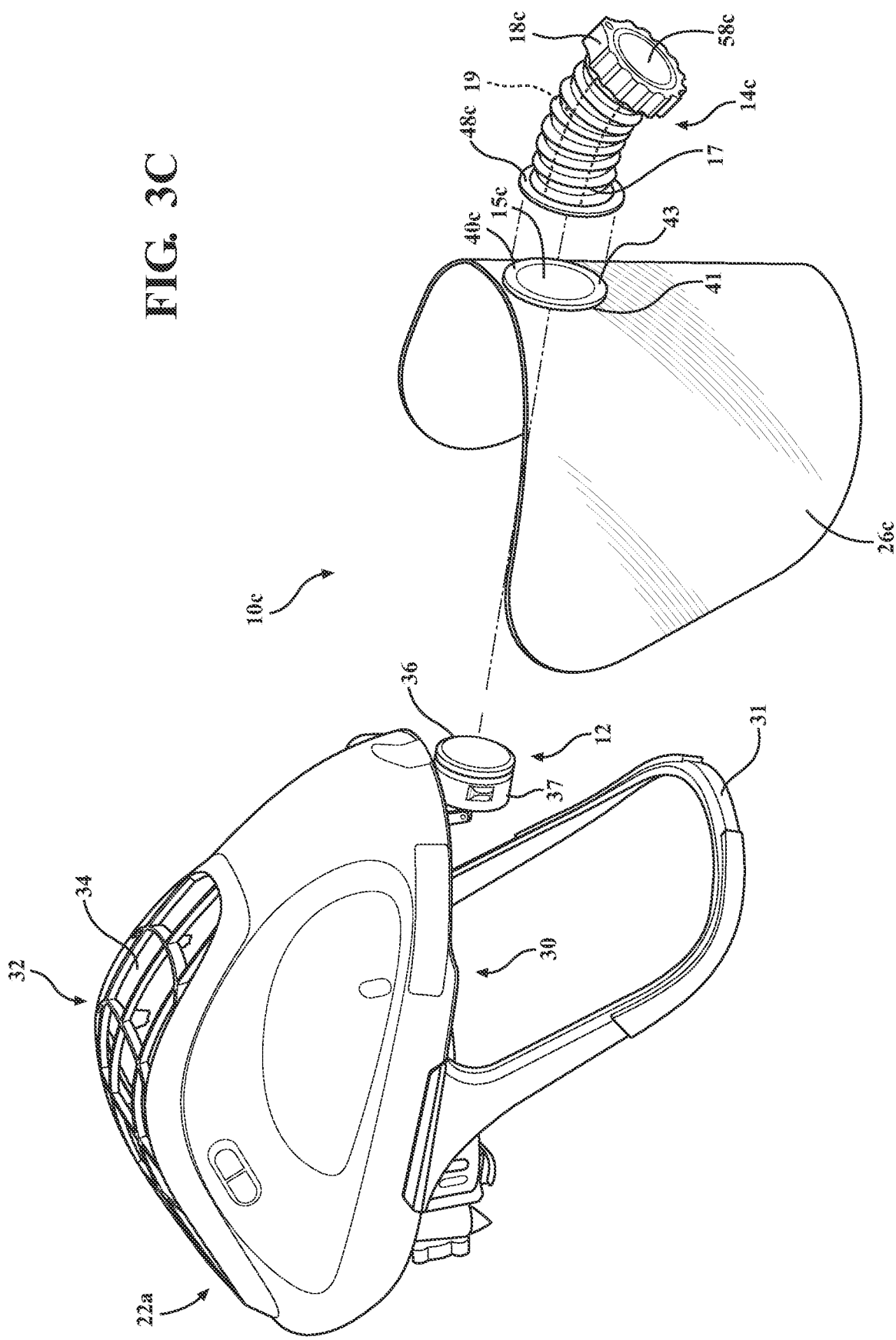
FIG. 3C is a partially exploded view of an exemplary configuration of the protective apparel system of FIG. 1A including a surgical helmet with a headlamp and a third configuration of a lens assembly.

Referring to FIGS. 3A-3C, various configurations of the lens assembly 14 for use with the surgical helmet 22 including a headlamp 12 are illustrated. The lens assembly 14 may comprise a housing 48A, 48B, 48C, that is configured to be at least partially disposed on the environment side of the protective apparel apparatus 10A. The housing 48A, 48B, 48C may be configured to be positioned proximate the face shield 26A, 26B and to engage a coupling member 40A, 40B, 40C to attach the lens assembly to the protective apparel apparatus 10A, 10B, 10C. This may be accomplished in a number of different ways depending on the type and or configuration of the protective apparel apparatus 10A, 10B, 10C. For example, the coupling member 40 may be configured to be disposed on and/or coupled to an interior surface on the face shield 26A on the wearer side of the protective apparel apparatus 10A. The housing 48 may then be configured to be disposed on and/or coupled to an exterior surface on the face shield 26A on the wearer side of the protective apparel apparatus 10A. Alternatively, it is also contemplated that the coupling member 40B and/or the housing 48B may be at least partially disposed within the opening 28 in the face shield. For example, a portion of the housing 48B may be at least partially disposed within the opening 28 of the face shield 26B such that the control member 18B, at least partially disposed on the wearer side, may couple to the housing 48B. In yet another configuration, a portion of the coupling member 40C may be at least partially disposed within the opening 28 of the face shield 26B such that the housing 48C, at least partially disposed on the environment side, may couple to the control member 18C. Exemplary configurations will be described in greater detail below with regard to FIGS. 3A-3C.

Referring to FIGS. 3A and 3B, the lens assembly 14A, 14B may generally comprise a control member 18A, 18B. The control member 18A, 18B may be disposed on the environment side of the protective apparel apparatus 10A, 10B and configured to engage the housing 48A, 48B of the lens assembly 14A, 14B. The control member 14A, 14B may also comprise a lens 58A, 58B configured to manipulate the direction and/or intensity of the light passing through the lens assembly 14A, 14B. The control member 18A, 18B may be manipulatable by the wearer, on the environment side, to direct and/or manipulate the intensity of the light from the headlamp 12 without having to break or compromise the sterile barrier. For example, the control member 18A, 18B may be configured to threadably engage the housing 48A, 48B such that the control member 18A, 18B may be rotated to manipulate the position of the control member 18A, 18B, and by extension the lens 58A, 58B, relative to the housing 48A, 48B and/or the headlamp 12. Alternatively, the control member 18A, 18B may be configured to slidably engage the housing 48A, 48B such that the control member 18A, 18B may be slid relative to the housing 48A, 48B to manipulate the position of the control member 18A, 18B, and by extension the lens 58A, relative to the housing 48A, 48B and/or the headlamp 12. The lens assembly 14A may be configured such that the manipulating the position of the control member 18A, 18B, and by extension the lens 58A, 58B, relative to the housing 48A, 48B and/or the headlamp 12 will adjust the direction and/or intensity of the light passing through the lens assembly 14A, 14B. This concept will be explained in greater detail below.

FIG. 3A illustrates a partially exploded view of a first configuration of a lens assembly 14A configured for coupling to the first configuration of the protective apparel apparatus 10A of FIG. 2A. The first configuration of the protective apparel apparatus 10A may comprise the first configuration of the face shield 26A. As described above, the face shield 26A does not include any exposed openings or apertures when the face shield 26A is coupled to the surgical garment 20 in order for the protective apparel apparatus 10A to form a solid sterile barrier. In such a configuration, a portion of the lens assembly 14A may be integrally formed with the face shield 26A and/or coupled to the face shield 26A. For example, the face shield 26A may be formed as unitary piece including the features of the housing 48A formed on the environment side of the face shield 26A. Wherein the housing 48A is formed as a portion of the face shield 26A, the housing 48A would include a lens 16A to maintain the sterile barrier created by the protective apparel apparatus 10A. Alternatively, it is contemplated that, the lens assembly 14 may be attached to the face shield 26A by an adhesive. In this configuration, a coupling member 40A may be adhere to the face shield 26A on the wearer side and housing 48A of the lens assembly 14 may be adhere to the face shield 26A on the environment side of the sterile barrier. In yet another configuration, the lens assembly 14 may be attached to the face shield 26A by magnetic attraction. For example, the face shield 26A may comprise a placement feature such as a recess or detent on the surface of the face shield 26A to assist with placement and/or positioning of the lens assembly. Each of the coupling member 40A and the housing 48A may have a similar feature configured to engage and/or mate with the placement feature on the respective surfaces of the face shield 26A. Each of the coupling member 40A and the housing 48A may also comprise one of a ferrous material or a magnetic material configured to create a magnetic attraction between the coupling member 40A and the housing 48A across the face shield 26A. For example, the coupling member 40A may comprise one of a ferrous material and a magnetic material and the housing 48A may comprise the other of a ferrous material and a magnetic material, such that when both the coupling member 40A and the housing 48A are position on their respective sides of the face shield 26A, the ferrous material and the magnetic material create a magnetic attraction between the coupling member 40A and the housing 48A that removably attaches the lens assembly 14A to the face shield 26A. Alternatively, it is contemplated that the face shield 26A may comprise one of one of a ferrous material and a magnetic material imbedding with the face shield 26A, and the control member 40A and the housing 48A may comprise the other of a ferrous material and a magnetic material to create a magnetic attraction between face shield 26A and the coupling member 40A and the housing 48A. The headlamp 12 may then be positioned proximate to and/or coupled to the coupling member 40A when the protective apparel apparatus 10A is disposed over the surgical helmet 22. Additionally, the control member 18A may be similarly configured to be manipulated in one of the methods described above to manipulate the direction and/or intensity of the light passing through the lens assembly 14A.

FIG. 3B illustrates a partially exploded view of a second configuration of a lens assembly 14B configured for coupling to the second configuration of the protective apparel apparatus 10B of FIG. 2B. As described above, the face shield 26B may comprise one or more openings or apertures 28B. The location and shape of the opening 28B, including any additional openings, may vary. Shape configurations may be any suitable shape such as a circle, oval, square or the like. For instance, the opening 28B proximate the center portion of the face shield 26B with a circular shape configuration. Furthermore, the protective apparel apparatus 10B may include other materials, different from the face shield 26, disposed within the opening 28B such that the additional materials of the face shield 26B spans the opening 28B. In such a configuration, the lens assembly 14B may be configured to couple with the face shield 26B via the opening 28B. For example, the coupling member 40B may be configured to couple to, or be partially disposed within, the opening 28B. The headlamp 12 may then be configured to couple with the portion of the coupling member 40B on the wearer side of the barrier formed by the protective apparel apparatus 10B. The housing 48B may then be configured to couple with the portion of the coupling member 40B disposed within the opening 28B of the protective apparel apparatus 10B. In this configuration, the control member 40B would include a lens or cover 15B to maintain the sterile barrier created by the protective apparel apparatus 10B. The control member 18B may be similarly configured to be coupled to the housing 48B and manipulated in one of the methods described above to manipulate the direction and/or intensity of the light passing through the lens assembly 14B.

Referring to FIG. 3C, a partially exploded view of a third configuration of a lens assembly 14C is illustrated. Similar to the previously described configurations of the lens assembly 14A, 14B, the third configuration of the lens assembly 14C may comprise a housing 48C configured to couple with a coupling member 40C to couple the lens assembly 14C to the face shield 26A, 26B of the protective apparel apparatus 10C. As illustrated in FIG. 3C, the protective apparel apparatus 10C may be configured such that the coupling member 40C is integrally formed with the face shield 26C. In this configuration, the coupling member 40C would include a lens or cover 15C to maintain the sterile barrier created by the protective apparel apparatus 10C. The coupling member 40C as integrally formed with the face shield 26C may be configured such that a portion 43 of the coupling member 40C is disposed on the wearer side of the face shield 26C to engage and/or couple with the headlamp 12. The coupling member 40C as integrally formed with the face shield 26C may also be configured such that a portion 43C of the coupling member 40C is disposed on the environment side of the face shield 26C to engage and/or couple with the housing 48C of the lens assembly 14C.

The lens assembly 14C may comprise a control member 18C including a lens 58C for manipulating the direction and/or intensity of the light passing through the lens assembly 14C. However, the lens assembly 14C may also comprise an adjustable portion 17. The adjustable portion 17 may be disposed between the control member 18C and the housing 48C and configured to allow the user to further manipulate the direction of the light passing through the lens assembly 14C. For example, the adjustable portion 17 may comprise a flexible arm such that allows the user may further manipulate the position and/or orientation of the control member 18C relative to the housing 48C, and by extension the direction of the light. The adjustable portion 17 may also comprise an extensible and/or collapsible arm that allows the user to further manipulate the distance between of the control member 18C and the housing 48 controlling the location that the light may exit the lens assembly 14C. An example of an adjustable portion 17 may include a semi-rigid sleeve or member with a fiber optic cable 19 at least partial disposed within adjustable portion 17. The adjustable portion 17 may configured to allow the user to manipulate the position of the control member 18C to direct and/or angle the light toward the surgical area. The adjustable portion 17 may be configured to keep the control member 18C and the fiber optic cable in a fixed position relative to the protective apparel apparatus 10C and/or the surgical helmet 22 until manipulated further by the user.

While various combinations of the lens assembly 14A, 14B, 14C, coupling member 40A, 40B, 40C, and housing 48A, 48B, 48C for use with a face shield 26A, 26B, 26C, they are not intended to be limiting. The combinations described above are merely exemplary configurations of the protective apparel apparatus 10A, 10B, 10C, and additional combinations for coupling the lens assembly 14A, 14B, 14C, coupling member 40A, 40B, 40C, and housing 48A, 48B, 48C with a face shield 26A, 26B, 26C utilizing the components described above are contemplated.

II. Lens Assembly

As described above, in order to maintain the sterile barrier between the wearer and the surrounding environment and to adjust a characteristic of the light during a surgical procedure, the protective apparel system 5 may comprise protective apparel apparatus 10 including a lens assembly 14 at least partially disposed on the environment side of the face shield.

Figure 4:
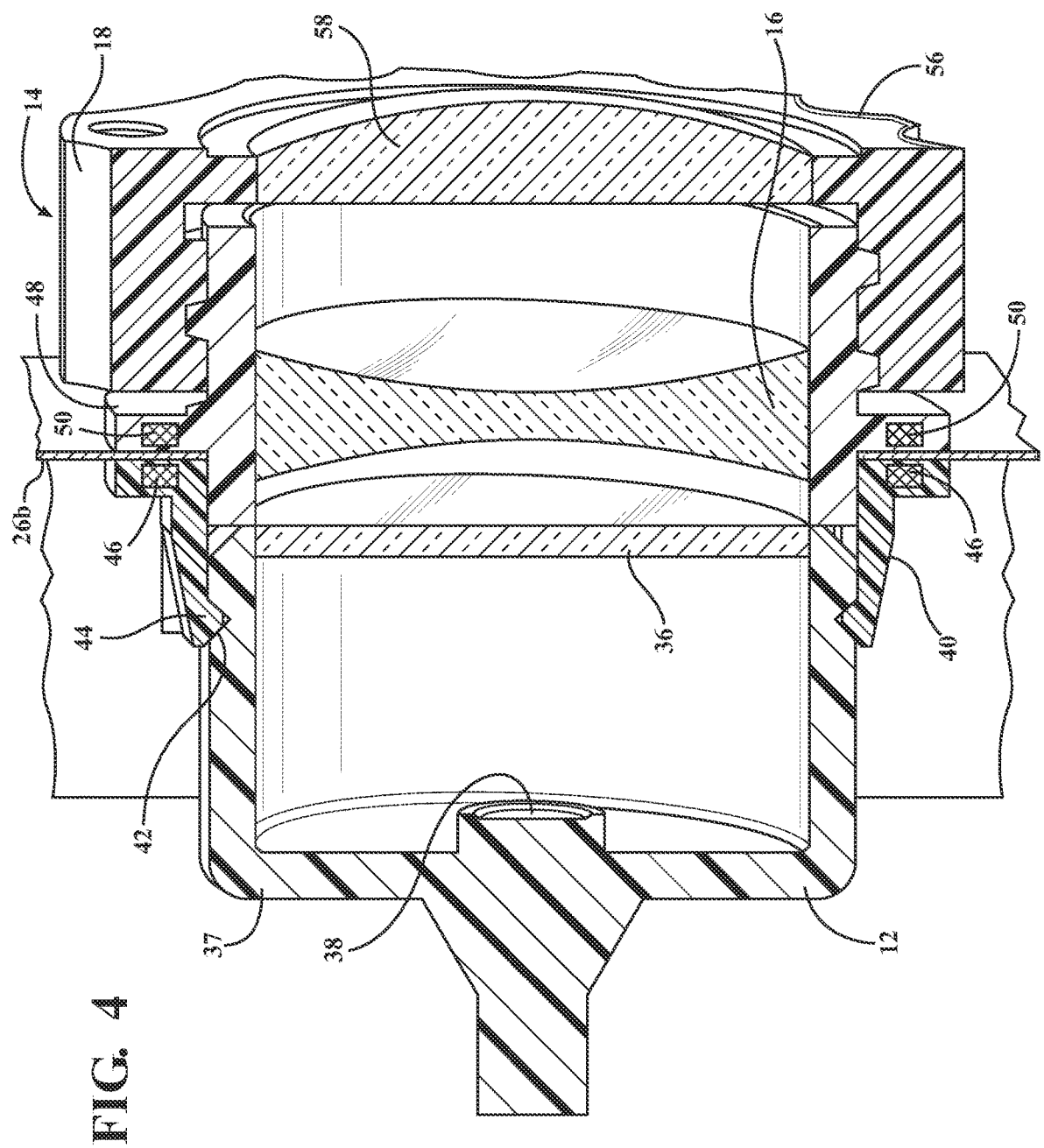
FIG. 4 is a cross-sectional view of a portion of the protective apparel system of FIG. 1A along line A-A.

Referring to FIG. 4, a cross-sectional view of a portion of the protective apparel system 5 of FIG. 1A along line A-A is illustrated. The protective apparel system 5 includes the headlamp 12 of the surgical helmet 22 coupled to the protective apparel apparatus 10B including a lens assembly 14B. As described above, the headlamp 12 may include a headlamp body 37. The headlamp body 37 may be formed in any suitable configuration. The headlamp 12 may also comprise a transparent cover 36 and a light source 38 at least partially disposed within the headlamp body 37. The transparent cover 36 may comprise a lens, screen, shield, or other similar cover mechanism configured to allow light to pass through. The transparent cover 36 may be configured to cover a headlamp opening defined by the headlamp body 37 in order to prevent dust, dirt, or moisture from entering into the inside of the headlamp 12, while also allowing light transmitted by the light source 38 to pass through. The transparent cover 36 may comprise any type of material, including, but not limited to, plastic, glass, and/or the like. Additionally, the transparent cover 36 may be a plain screen, without any optically active elements, or a diffuser lens, with optically active elements such as cylindrical lenses, spherical lenses, Fresnel lenses, prisms and the like. In one configuration, the headlamp 12 may comprise any number of screens, lens, and/or reflectors.

The headlamp body 37 may further comprise a mounting feature 42 configured to couple with the coupling member 40. The coupling member 40 may comprise a coupling feature 44 such that the mounting feature 42 of the headlamp 12 and the coupling feature 44 of the coupling member are configured to engage each other when the coupling feature 40 and the headlamp 12 are coupled together. For example, the mounting feature 42 of the headlamp 12 may be configured to matingly engage a complementary coupling feature 44 of the coupling member 40. The mounting feature 44 and the coupling member 40 may be any configuration, including, but not limited to, a snap fit or detent connection, a magnetic connection, threaded connection, and the like. For example, as shown in FIG. 4, a coupling feature 44 may comprise an arm projecting from the coupling member 40 that includes a detent. The detent of the coupling feature 44 may be configured to engage the mounting feature 42 of the headlamp 12 that includes a recess or notch to removably couple the coupling member 40 and headlamp 12.

Alternatively, while not illustrated in the figures, it is also contemplated that the coupling member 40 and/or the lens assembly 14 may be configured to couple to the helmet 22. As illustrated in FIG. 1C, it is contemplated that the helmet 22B may comprise a mounting feature 45. In this configuration, the headlamp 12 may be mounted to the mounting feature 45 of the helmet 22B as described above. The coupling feature 44 of coupling member 40 may then be configured to be coupled directly to the headlamp 12, to the mounting feature 45 of the helmet 22B, or some combination thereof, such that the headlamp 12 is aligned with the lens assembly 14 when the coupling member 40 and/or the lens assembly 14 is mounted to the helmet 22B via the mounting feature 45. For example, the coupling feature 44 of the coupling member 40 may be configured to mate with the mounting feature 45 of the helmet 22B such that the coupling member 40 is coupled to the helmet 22. In this configuration, a headlamp 12 may also couple to the mounting feature 45 of the helmet 22B such that the coupling member 40 and the headlamp 12 are aligned. In such a configuration, the coupling member 40 may abut the inner surface of the face shield 26 when the protective apparel apparatus 10 is disposed over the helmet 22B. It is also contemplated that the headlamp 12 may be removably coupled to the mounting feature 45 of the helmet 22B, and the coupling member 40 of the lens assembly 14 may be coupled to the headlamp 12 in a similar manner as described above with regard to headlamp 12 and lens assembly 14 of FIG. 4.

In the configurations contemplated above, the coupling member 40 may be disposable and/or reusable. For example, the coupling member 40 may be removably coupled to allow for disposal of the protective apparel apparatus 10 and reuse of the surgical helmet 22 following a procedure or exam. Alternatively, it is also contemplated that the coupling member 40 may be permanently coupled to the protective apparel apparatus 10 and is disposed of following a procedure or exam.

The lens assembly 14 may also comprise a housing 48 and a control member 18 disposed on the environment side of the protective apparel apparatus 10. The housing 48 may be integrated with or permanently affixed to the face shield 26 in any suitable method. For example, the housing 48 may be integrated as a single unit with the face shield 26 of the surgical garment 20. In this configuration, the housing 48 may be coupled to the environment side of the face shield 26 using an adhesive such that the housing 48 will be aligned with the headlamp 12/coupling member 40 on the wearer side of the surgical garment 20 when the protective apparel apparatus 10 is disposed over the helmet 22. Suitable methods of permanently coupling the housing 48 of the lens assembly 14 to the environment side of the shield 26 may include, but is not limited to, welding, adhesion, or the like. In this configuration, other components of the lens assembly 14 may be removable. For example, the control member 18 may be removed and reused. Alternatively, it is also contemplated that the housing 48 may be removably coupled to the protective apparel apparatus 10. For example, the housing 48 may be coupled to the protective apparel apparatus 10 via an intermediary connecting material such as a hook and loop material, straps, or by snaps and the like. In this configuration, a hook portion may be disposed on the housing 48 and a loop portion may be disposed on the face shield 26, or vice versa. It is also contemplated that the in the configuration of the protective apparel apparatus 10B wherein the face shield 26B including the opening 28, the housing 48B may comprise a retention feature configured to create a friction fit or other similar connection with the opening 28B in the face shield 26B. In yet another configuration, the housing 48B may comprise a retention feature configured to extend through the opening 28B in the face shield 26B and coupled to the coupling member 40B.

In configurations wherein the face shield 26B comprises an opening 28, the housing 48B and/or the coupling member 40B may comprise a lens or cover to provide a solid barrier with the face shield 26B. For example, as illustrated in FIG. 4, the housing 48 may be permanently coupled to the face shield 26 and comprise a lens 16 so that there are not breaks or openings in the barrier provided by the protective apparel apparatus 10. In this configuration, the coupling member 40 may be removably coupled to the housing 48 and/or the face shield 26. Alternatively, while illustrated in FIG. 4, it is also contemplated that coupling member 40 may comprise a lens/cover and be permanently coupled to the face shield 26 so that there are not breaks or opening in the barrier provided by the protective apparel apparatus 10. In this configuration, the housing 48 may be removably coupled to the coupling member 40 and/or the face shield 26B.

The lens assembly 14 may further comprise one more lenses 16, 58. As illustrated in FIG. 4, the lens assembly 14 may comprise a first lens 16 and a second lens 58. The first lens 16 may be coupled to the housing 48, and the second lens 58 may be coupled to the control member 18 of the lens assembly 14. The first lens 16 and the second lens 58 may be configured to fit snugly in the housing 48 and the control member 18, respectively. As described above, the control member 18 may be configured to be manipulatable by the user. The control member 18 and the housing 48 may be coupled together such that manipulation of the control member 18 moves the control member 18 and, by extension, the second lens 58, relative to the housing 48 and, by extension, the first lens 16. The control member 18 may be configured such that the wearer may easily manipulate the control member 18 to adjust a position of the second lens 58 relative to the first lens 16 by rotating, sliding, or similarly manipulating the control member 18.

Depending on the type of manipulation of the control member 18 and/or the coupling between the housing 48 and the control member 18, a characteristic of the lens assembly 14 is adjusted. In one example, manipulation of the control member 18 may vary the distance or position of the first lens 16 and/or the second lens 58. Varying a distance from the first lens 16 and the second lens 58 varies the light from the headlamp 12 to a desired focal point 74. Alternatively, varying a distance from the first lens 16 and the second lens 58 may vary the light path from the headlamp 12. The desired focal point 74 may include, but not limited to, the workspace or an area of interest. Alternatively, varying a distance or position of the lens 16, 58 may vary the light path from the headlamp 12. In another example, manipulation of the control member 18 may vary an angle of the light emitted from the headlamp. In this example, the housing 48 may comprise reflectors, fiber optic cables, and the like. In an exemplary configuration, as illustrated in FIG. 3C, the lens assembly 14 may be extendable or movable such that manipulation of the control member 18 by the wearer varies the light angle. In this configuration, the housing 48 may comprise fiber optic cables, reflectors or the like to aid in varying light angle. For instance, in combination with the use of any number of reflective surfaces or fiber optic cables, the light from the headlamp 12 may be redirected or articulated such that the surgical field, workspace, and/or patient is illuminated. It will be appreciated that the other characteristics of the lens assembly 14 may include, but not limited to, adjusting the total internal reflection of the lens assembly 14.

While the sectional view of FIG. 4 illustrates an exemplary lens assembly 14 including a first lens 16 and a second lens 58, it is contemplate that the lens assembly 14 may comprise any number of lenses. For example, while not illustrated in the figures, it is contemplated that the lens assembly 14 may comprise only one (first) lens 16. Furthermore, it is contemplated the system 5 may include any number of additional lenses. For example, the lens assembly 14 may also comprise a screen or cover similar to the transparent cover 36 of the headlamp 12 described above. It is also contemplated that the headlamp 12 may include additional lenses, such as the transparent cover 36, wherein the combination of the headlamp 12, lens assembly 14 and the transparent shield 26 comprise a system/assembly including a plurality of lenses working together to modify the direction and/or intensity of the light produced by the headlamp 12. In some configurations, the "first" lens and the "second" lens may be interchangeable. For example, the headlamp 12 may comprise the "first" lens and the lens assembly 14 may comprise the "second" lens and vice versa.

Referring to FIG. 5A-6B, two exemplary configurations of the lens assembly 14A, 14B for use with a headlamp 12 are illustrated. As described above, the lens assembly 14A, 14B may comprise a coupling member 40A, 40B. The coupling member 40A, 40B may comprise any suitable shape, such as circular, oval, or polygonal shapes. The coupling member 40A, 40B may include a recess having various shapes and/or sizes in which light generated from the headlamp 12 may pass through.

Figure 5A:
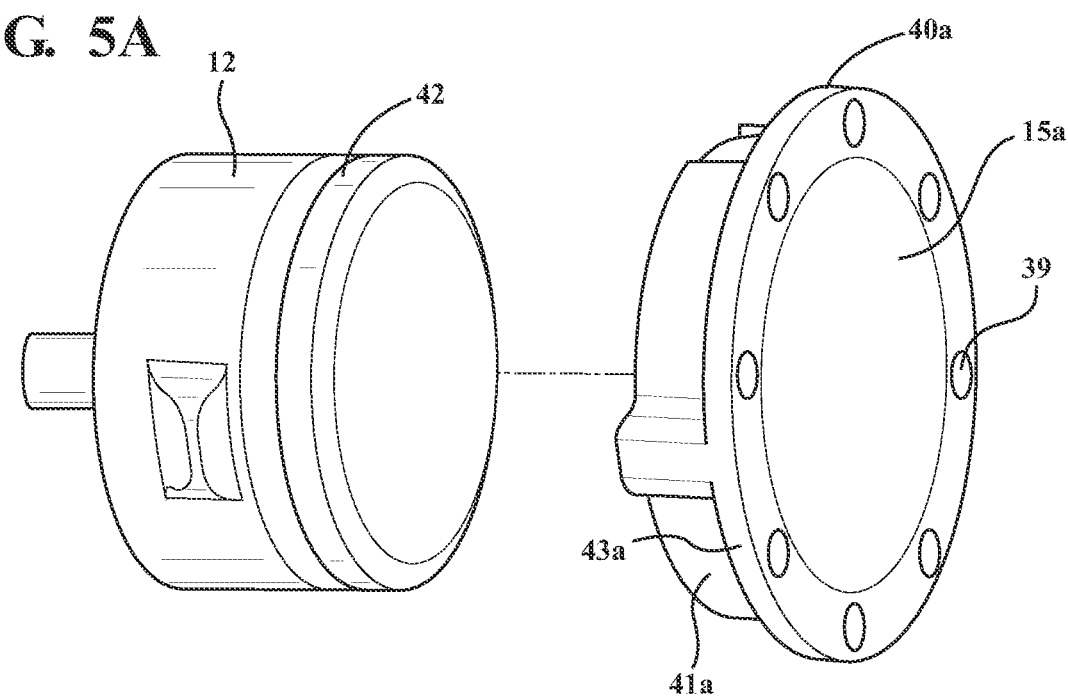
FIG. 5A is a partially exploded view of an exemplary configuration of a headlamp and a coupling member for use with the first configuration of the surgical garment and the lens assembly of FIG. 3A.
Figure 5B:
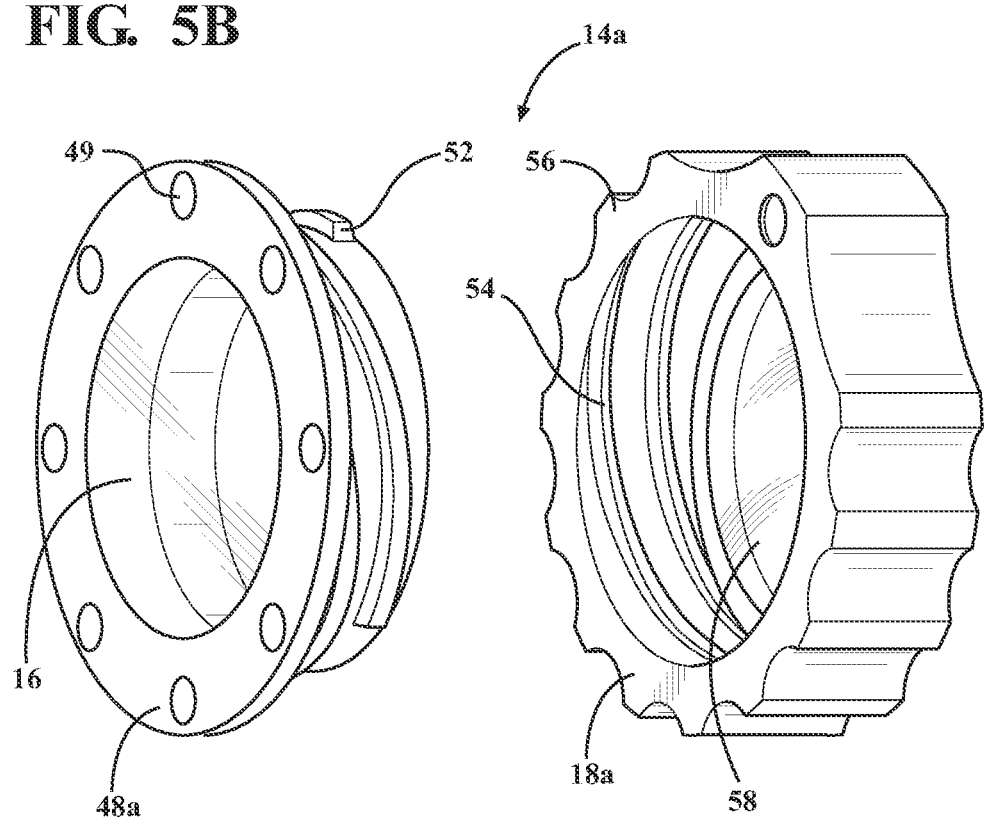
FIG. 5B is a partially exploded view of the first configuration of the lens assembly of FIG. 3A, the lens assembly including a housing, a first lens, a second lens, and a control member.

Referring to FIGS. 5A and 5B, a first configuration of the lens assembly 14A and a first configuration of the coupling member 40A wherein the coupling member 40B may have an inner portion 41A and an outer portion 43A with the inner portion 41A including a mounting feature 44A for coupling to the headlamp 12. The coupling member 40A may be configured to be couple with the first configuration of the protective apparel apparatus 10A including the face shield 26A, as illustrated in FIGS. 2A and 3A. In this configuration the face shield 26A does not include any exposed openings. The outer portion 43A of the coupling member 40A may abut the wear side of the face shield 26A. As described above, the coupling member 40A may comprise a retention feature 39A for coupling the coupling member 40A to the face shield 26A. The retention feature 39A may comprise a magnet, hook and loop, adhesive, or similar fastener. The face shield and/or housing 48A may then comprise a corresponding retention feature 48A. For example, the coupling member 40A may comprise a retention feature 39 including a ferrous material and the housing 48A may comprise a retention feature 49 including a magnetic material, such that when both the coupling member 40A and the housing 48A are position on their respective sides of the face shield 26A, the ferrous material and the magnetic material create a magnetic attraction between the coupling member 40A and the housing 48A that removably attaches the lens assembly to the face shield 26A. Alternatively, it is contemplated that the coupling member 40A may comprise a retention feature 39A including a magnetic material and the face shield may comprise a ferrous material imbedding with the face shield 26A such that the ferrous material and the magnetic material create a magnetic attraction between the coupling member 40A and the face shield 26A. In this configuration, the housing 48A may similarly comprise a retention feature 49 including a magnetic material such that the ferrous material imbedded in the face shield 26A and the magnetic material of the housing 48A create a magnetic attraction between the housing 48A and the face shield 26A.

Figure 6A:
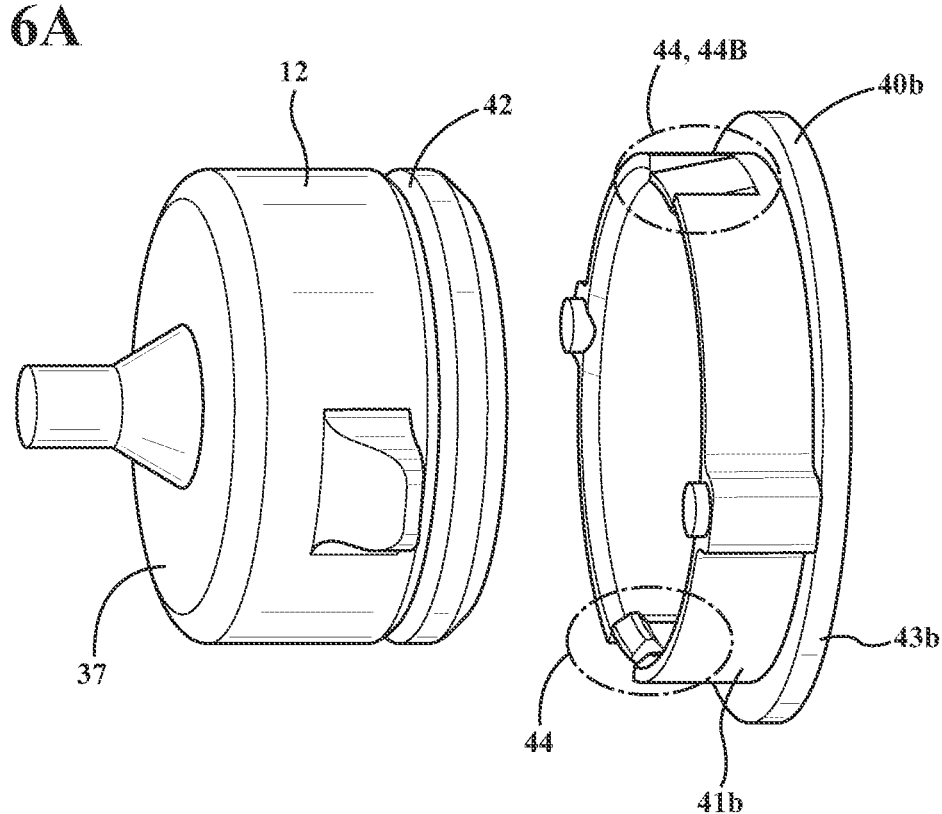
FIG. 6A is a partially exploded view of an exemplary configuration of a headlamp and a coupling member for use with the second configuration of the surgical garment and the lens assembly of FIG. 3B.
Figure 6B:
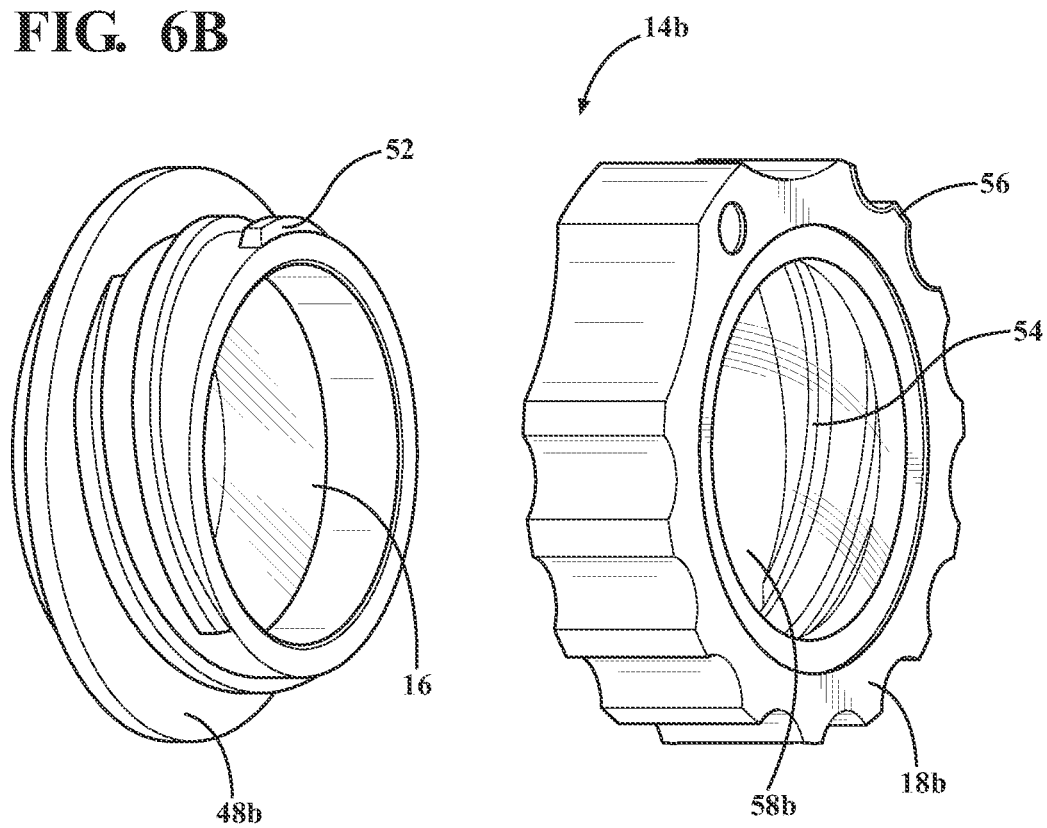
FIG. 6B is a partially exploded view of the second configuration of the lens assembly of FIG. 3B, the lens assembly including a housing having a coupling feature, a first lens, a second lens, and a control member.

Referring to FIGS. 6A and 6B, a second configuration of the lens assembly 14B and a second configuration of the coupling member 40B wherein the coupling member 40B may have an inner portion 41B and an outer portion 43B with the inner portion 41B including a mounting feature 44B for coupling to the headlamp 12. The coupling member 40B may be configured to be couple with the second configuration of the protective apparel apparatus 10B including the face shield 26B with an opening 28B, as illustrated in FIGS. 2B and 3B. The outer portion 43B of the coupling member 40B may abut the wear side of the face shield 26B and the aperture defined by the coupling member 40B may generally encircle the opening 28B. Alternatively, the coupling member 40B need not encircle the opening 28B. For example, the coupling member 40B may comprise one or more individual tabs coupled to the wearer side of the face shield 26B proximate to the opening 28B. The housing 48B may be coupled to the face shield 26B and comprise a lens configured to cover the opening. The plurality of tabs may configured to couple to the headlamp 12 in order to align the headlamp with the housing 48 and/or the lens assembly 14B. The coupling member 40B may have other configurations other than what is shown in the figures and described herein.

As mentioned above, the coupling member 40 may couple to the headlamp 12, the helmet 22, and/or the face shield 26. It is also contemplated that the coupling member 40 is configured to couple to the lens assembly 14. In each of the configurations described above, it is contemplated that the coupling member 40 and/or the lens assembly 14 may be disposable and/or reusable. For example, the coupling member 40 may be removably coupled to allow for disposal of the surgical garment 20 and face shield 26 portions of the protective apparel apparatus 10 and reuse of the coupling member 40 following a sterilization procedure/process. Alternatively, the coupling member 40 may be permanently coupled to the face shield 26 such the coupling member 40 is disposed of with the protective apparel apparatus 10 following a procedure or exam. It is also contemplated that portions of the lens assembly 14 may be reusable while other portions are disposable. For example, the housing 48 and/or control member 18, which may be removable in certain configurations of the protective apparel apparatus 10, may be configured to be reusable. Alternatively, the housing 48 portion of the lens assembly 14 may be permanently coupled to the protective apparel apparatus 10 and may be disposed of with the surgical garment 20 and face shield 26 portions of the protective apparel apparatus 10.

In configurations wherein a solid barrier is provided, the lens assembly 14 may be reusable with another surgical garment 20. Referring to FIG. 2C, the wearer may use the lens assembly 14 with one surgical garment 20, remove the lens assembly 14, and then use the lens assembly 14 with another surgical garment 20. It will be appreciated that any or all components of the lens assembly 14 may be reusable. Additionally, the lens assembly 14 may be sterilized between each usage and/or removal of the lens assembly 14 in order to maintain the sterile barrier.

In some configurations wherein the face shield 26B comprises an opening 28B, as shown in FIG. 2B, the coupling member 40 may comprise a cover similar to the transparent cover 36 of the headlamp 12 as mentioned above or a lens similar to the first lens 16. The coupling member 40 in combination with the cover or lens may form the sterile barrier in conjunction with the face shield 26 and the rest of the surgical garment 20. Further, in these configurations, the coupling member 40 is attached to the face shield 26. In other configurations, the housing 48 in combination with the first lens 16 may form the sterile barrier with the face shield 26. In these configurations, components such as the control member 18 of the lens assembly 14 may be reusable and/or removable. Referring to FIG. 3B, the housing 48B may be constructed and attached to the surgical garment 20B about the opening 28B such that bacteria cannot enter or exit through the opening 28B once the housing 48 abuts and/or is coupled to the face shield 26B. In these configurations, the lens assembly 14 may be reusable and/or removable without breaching the sterile barrier.

In yet other configurations wherein the face shield 26 may not comprise any openings, as shown in FIGS. 2A and 3A, the face shield 26 provides a solid barrier between the environment side and the wearer side. In these configurations, any or all components of the lens assembly 14 may be reusable, removable, and/or disposable as mentioned above. Removing any of the aforementioned components will not break the sterile barrier between the environment side and the wearer side as a solid barrier is provided by the face shield 26, the coupling member 40, and/or the headlamp 12.

The sterile barrier is arranged between the wearer side and the environment side of the surgical garment 20. Any microbes or other contamination (e.g. dust, particulate matter, other biological matter, etc.) that is introduced during a surgical procedure will remain on the environment side of the surgical garment 20 and/or remain on the wearer side of the surgical garment 20.

In certain configurations, a significant advantage of the lens assembly 14 is that the sterile barrier is designed as a continuous, solid barrier that is maintained throughout any manipulation of the control member 18 of the lens assembly 14. Such a solid barrier can be provided because, in one example, the housing 48 in combination with the lens 16 of the lens assembly 14 is adapted to form a part of the sterile barrier such that the sterile barrier may extend unbroken between the housing 48 and the face shield 26. Thus, any manipulation of the lens assembly 14 during a surgical procedure does not compromise the sterile barrier between the wearer and the environment.

As mentioned above, the coupling member 40 may be coupled to the lens assembly 14 by an attachment feature 46. More specifically, the coupling member 40 may be coupled to the housing 48 of the lens assembly 14 with the attachment feature 46. The housing 48 may comprise a (mating) attachment feature 50 such that the attachment feature 46 and the mating attachment feature 50 are attached to each other. For example, as shown in FIG. 4, the attachment feature 46 may comprise a ferrous material and the mating attachment feature 50 of the housing 48 is a magnet, or vice versa. When the attachment feature 46 contains material that is capable of being attracted to a magnetic material, the mating attachment feature 50 of the housing 48 can, in addition or alternatively, include magnetic components. In other words, the attachment feature 50 may comprise a permanent magnetic material and the complementary element, in this example is attachment feature 46 of the coupling member 40, comprises a ferrous material or vice versa. In this manner, the housing 48 of the lens assembly 14 can be secured to the coupling member 40, at least in part, magnetically.

The mating attachment feature 50 may be coupled to any component of the lens assembly 14 such that mating attachment feature 50 is attached to the attachment feature 46 of the coupling member 40. Further, the attachment feature 50 may be attached to the coupling member 40 in any suitable manner such that the sterile barrier between the wearer side and the environment side is maintained.

Another example, the attachment feature(s) may comprise a press or shrink fit whereby there is an interference fit between the coupling member 40 and the housing 48 in which one of the two elements is forced under pressure into the other element through the surgical garment in a way sufficient to maintain a sterile barrier. It will be appreciated that the attachment feature(s) 46, 50 may be any type of attachment, including, but not limited to, threading, adhering, mechanical fastening, and/or pressure fitting. Alternatively, both the coupling member 40 and the housing 48 may be permanently attached to the face shield 26.

In some configurations, the mounting feature 44 of the coupling member 40 and the attachment feature 46 may be a single unit or component such that the mounting feature 44 and the attachment feature 46 are the same feature configured to mount both the headlamp 12 and the lens assembly 14 simultaneously. For example, the coupling member 40 is a magnet. The magnet may be positioned proximate to the opening 28. The mounting feature 44 and the attachment feature 46 mounts to the headlamp 12 and the lens assembly 14, respectively, through magnetic force. In other words, the mounting feature 44 and the attachment feature 46 is the same feature (magnetic force) of the coupling member 40.

Alternatively, the mounting feature 44 and the attachment feature 46 may be different and/or separate features of the coupling member 40.

Furthermore, the housing 48 is configured to couple to the control member 18 as shown throughout the Figures. The housing 48 may couple to the control member 18 in any suitable method. The control member 18 may be manipulated by the wearer to move relative to the housing 48. Various configurations of the control member 18 and techniques of manipulation are contemplated in detail below.

In one configuration, as shown in FIG. 6B, the housing 48 may comprise a plurality of external threads 52 at one axial end thereof for threadably engaging internal threads 54 in a cavity of the control member 18. The external and internal threads 52, 54 may be right-handed threads or left-handed threads. In this configuration, the wearer may manipulate the control member 18 by rotating the control member 18 relative to the housing 48 such that the external threads 52 engages the internal threads 54 of the control member 18 whereby moving the control member 18 relative to the housing 48. Depending on the direction of the rotation, the control member 18 may be manipulated to move towards or away from the housing 48.

In another configuration, the control member 18 may include a motion or gesture detector. For example, to manipulate the control member 18, the wearer may perform a motion such as a finger swipe on the control member 18. In this configuration, the control member 18 may include any number of sensors or detectors.

In another configuration, the control member 18 may be slidably engaged relative to the housing 48 of the lens assembly 14. In other words, to manipulate the control member 18, the wearer may slide an element of the control member 18 or the entirety of the control member 18 relative to the housing. For example, the control member 18 may be slidably engaging the housing 48 such that the wearer may slide the control member 18 forwards, backwards, upwards, or downwards relative to the housing 48 to alter one or more characteristics of the lens assembly 14.

In another configuration, the control member 18 may take the form of a handle, lever, button or the like. To manipulate the control member 18, the wearer may apply force or pressure thereto. For example, the control member 18 may include directional buttons wherein if the wearer presses a directional button, a component of the lens assembly 14 may move to the corresponding direction to alter a characteristic of the lens assembly 14.

In another configuration, the control member 18 may be remotely manipulatable via a controller. Additionally, an input device may be in communication with the control member 18 and the controller such that the input device may be utilized to manipulate the control member 18. Input devices may include, but not limited to, a display screen with touch screen capabilities, a joystick, a keyboard, a microphone, and a scanner.

In another configuration, the housing 48 may be formed such that the housing 48 and the control member 18 are not readily separable from one another once assembled. For example, the housing 48 may comprise retainer posts adapted to snap fit within the cavity of the control member 18.

In yet another configuration, the housing 48 may include the control member 18 such that the housing 48 and the control member 18 are integrated into a single component or unit. In this example, the housing 48 may be integrated with the control member 18 during manufacture of the lens assembly 14. Alternatively, the housing 48 may be separately manufactured from the control member 18 and wherein once the housing 48 engages the control member 18, the components 18, 48 are inseparable.

Additionally, the control member 18 may comprise a gripping feature 56 designed to enable the wearer to easily manipulate the control member 18. For example, the gripping feature 56 may be grooves formed on the control member 18. In operation, the wearer may grip the control member 18 along the grooves 56 and manually couple the control member 18 to the housing 48. The wearer may rotate the control member 18 towards to the housing 48 such that, in one configuration, the internal threads 54 of the control member 18 threadably engage the external threads 52 of the housing 48.

Figure 7B:
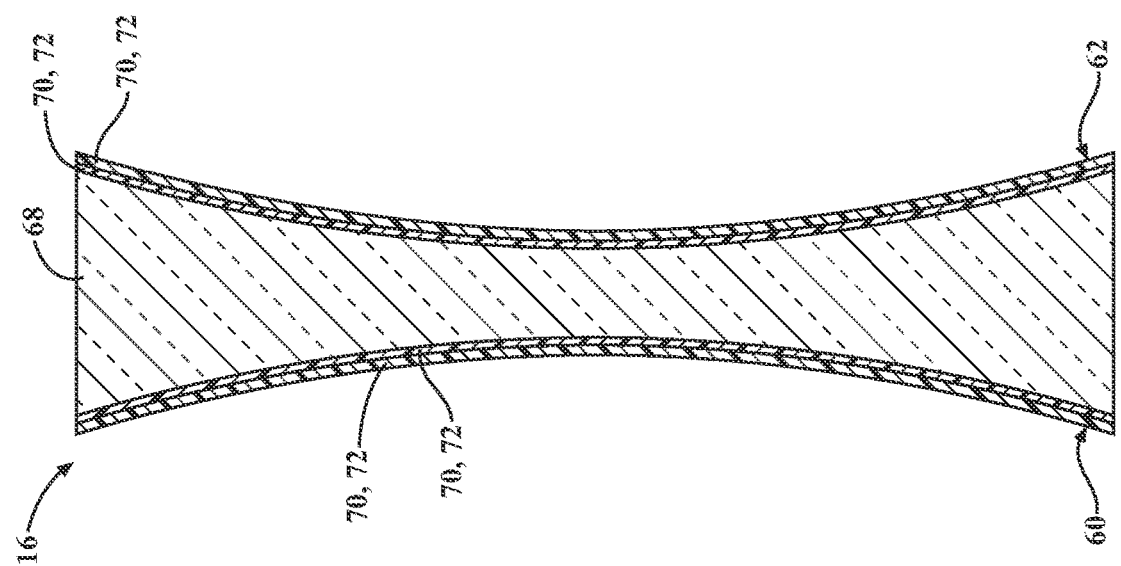
FIG. 7B is a cross-sectional view of the layers of a second lens for use with a lens assembly.
Figure 7A:
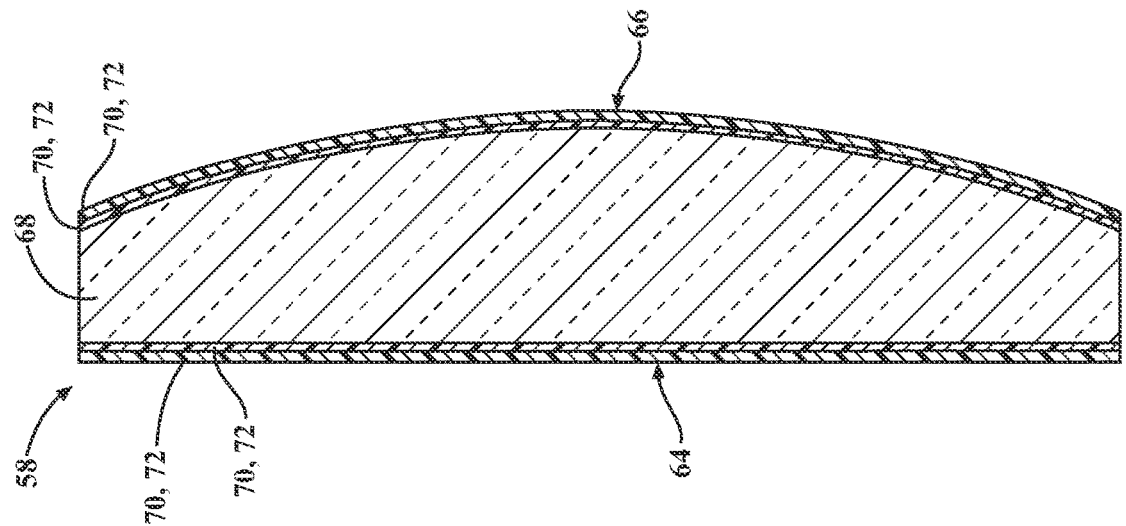
FIG. 7A is a cross-sectional view of the layers of a first lens for use with a lens assembly.

Referring to FIGS. 7A and 7B, the first lens 16 and the second lens 58 of the lens assembly 14 may each independently comprise any number of surfaces of any varying forms, including, but not limited to, convex, concave, and concave-convex (shaped) surfaces. As shown throughout the Figures, the first lens 16 may comprise two surfaces 60, 62 and the second lens 58 may comprise two surfaces 64, 66. In one configuration, the surface 60 of the first lens 16 may be a convex surface and the surface 62 may be a concave surface or vice versa. In another configuration, the surface 60 of the first lens 16 may be a convex surface and the surface 62 may be a flat surface or vice versa. As illustrated in FIGS. 7A and 7B for exemplary purposes, in another configuration, the first lens 16 is a dual concave lens with surfaces 60, 62 curving inwards and the second lens 58 is a dual convex lens with surfaces 64, 66 curving outwards. The surfaces 60, 62, 64, 66 of the first and second lenses 16, 58 may be any combination of surfaces.

The first lens 16 and/or the second lens 58 may be made in form of a reflector (e.g. mirror) which reflects the light by common reflection, or as a translucent body made of glass or plastic material (optical lens) where the focusing of light is achieved by optical refraction. In one configuration, the first and second lenses 16, 58 comprise a lens material 68 formed of a translucent body of glass or plastic material. The lens material 68 may be stiff or flexible. Additionally, the material 68 may be made of acrylate or polystyrene, or comparable low-cost but durable transparent material having suitable refractive properties.

A film 70 and/or a coating 72 may be disposed on any of the surfaces 60, 62, 64, 66 or any other surface of the first and second lenses 16, 58. Alternatively, the film 70 may be disposed between the surfaces 60, 62, 64, 66 of the first and/or second lenses 16, 58. As shown in FIGS. 7A and 7B, according to one example, both the surfaces 60, 62, 64, 66 of the first and second lenses 16, 58 are layered with the film 70 and the coating 72. The surfaces 60, 62, 64, 66 may include any number of layers of film 70 and/or coating 72 in which the layers of film 70 and/or coating 72 may vary in thickness. It will be appreciated that the film 70 and/or the coating 72 may be on any surfaces 60, 62, 64, 66 of the first lens 16 and/or second lens 58. For example, the film 70 and coating 72 may be on only one of the surfaces 60, 62 of the first lens 16. It will further be appreciated that the layering order of the film 70 and the coating 72 may vary depending on the optimal layering order desired.

The film 70 may be of plastic material or glass and can be a plain sheet, without any optically active elements, or a diffuser lens, with optically active elements such as a cylindrical lenses or prisms. Additionally, the film 70 and/or the coating 72 may alter the way in which the lenses reflects and transmits light from the headlamp 12. Further, the film 70 may be any type of film, including, but not limited to, polarized film and metalized film.

The coating 72 may be any type of coating, including, but not limited to, tint coating, gradient coating, glass coating, plastic coating, anti-reflective coating, scratch-resistant coating, ultra-violet coating, hydrophobic coating, color coating, and mirror coating. The coating may be coated by any conventional method, such as roll coating, gravure coating, bar coating, or extrusion coating. In some configurations, the film 70 and the coating 72 may be understood as a single layer wherein the coating 72 is a coating composition for forming the film 70.

Figure 8B:
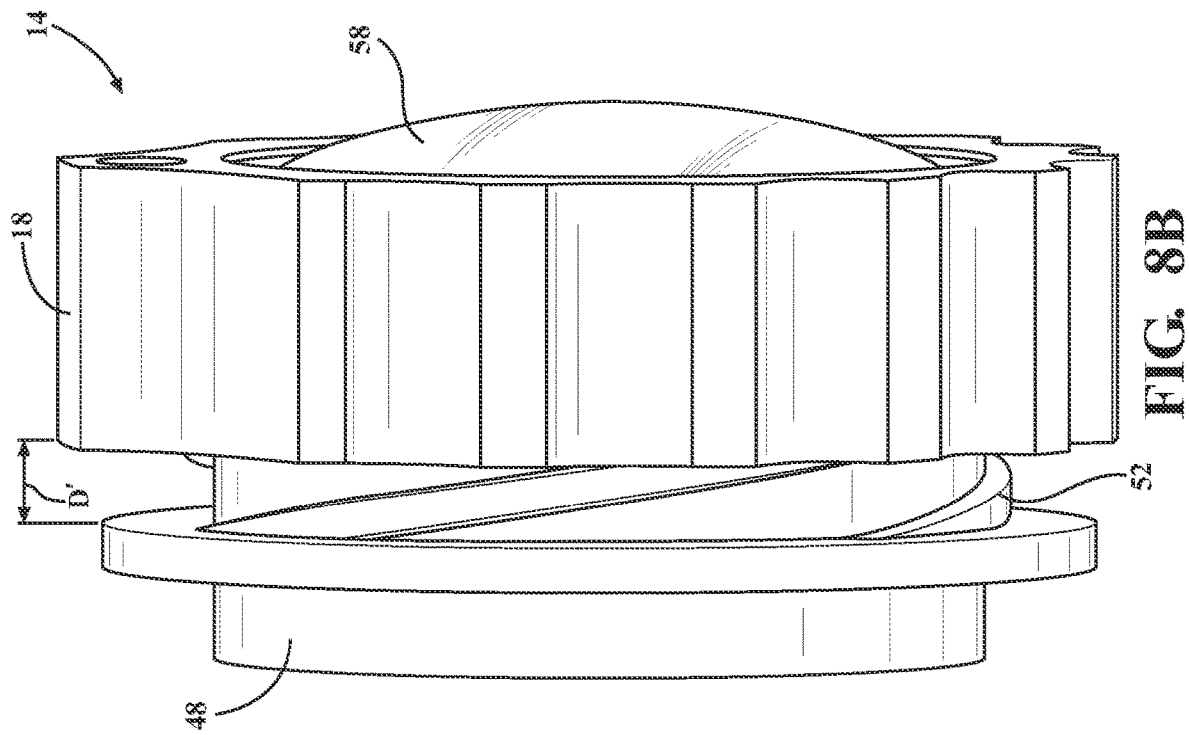
FIG. 8B is a perspective view of the second configuration of the lens assembly of FIGS. 3B and 4, illustrating the control member positioned at a second distance away from the housing.
Figure 8A:
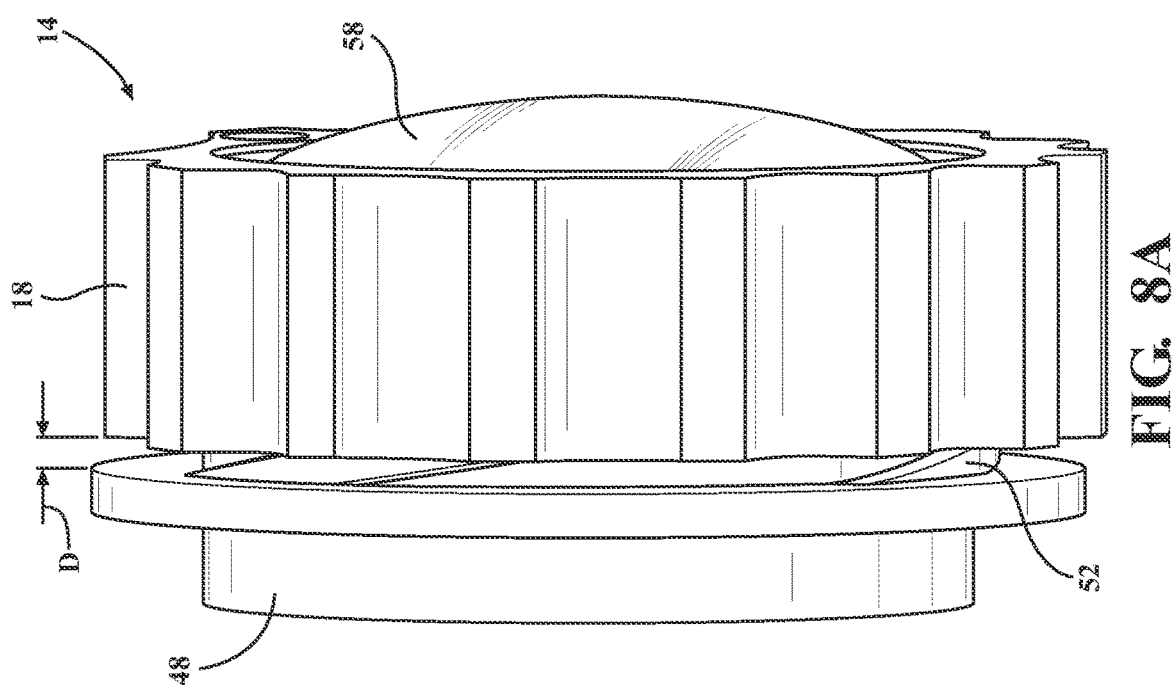
FIG. 8A is a perspective view of the second configuration of the lens assembly of FIGS. 3B and 4, illustrating the control member positioned at a first distance away from the housing.
Figure 8C:
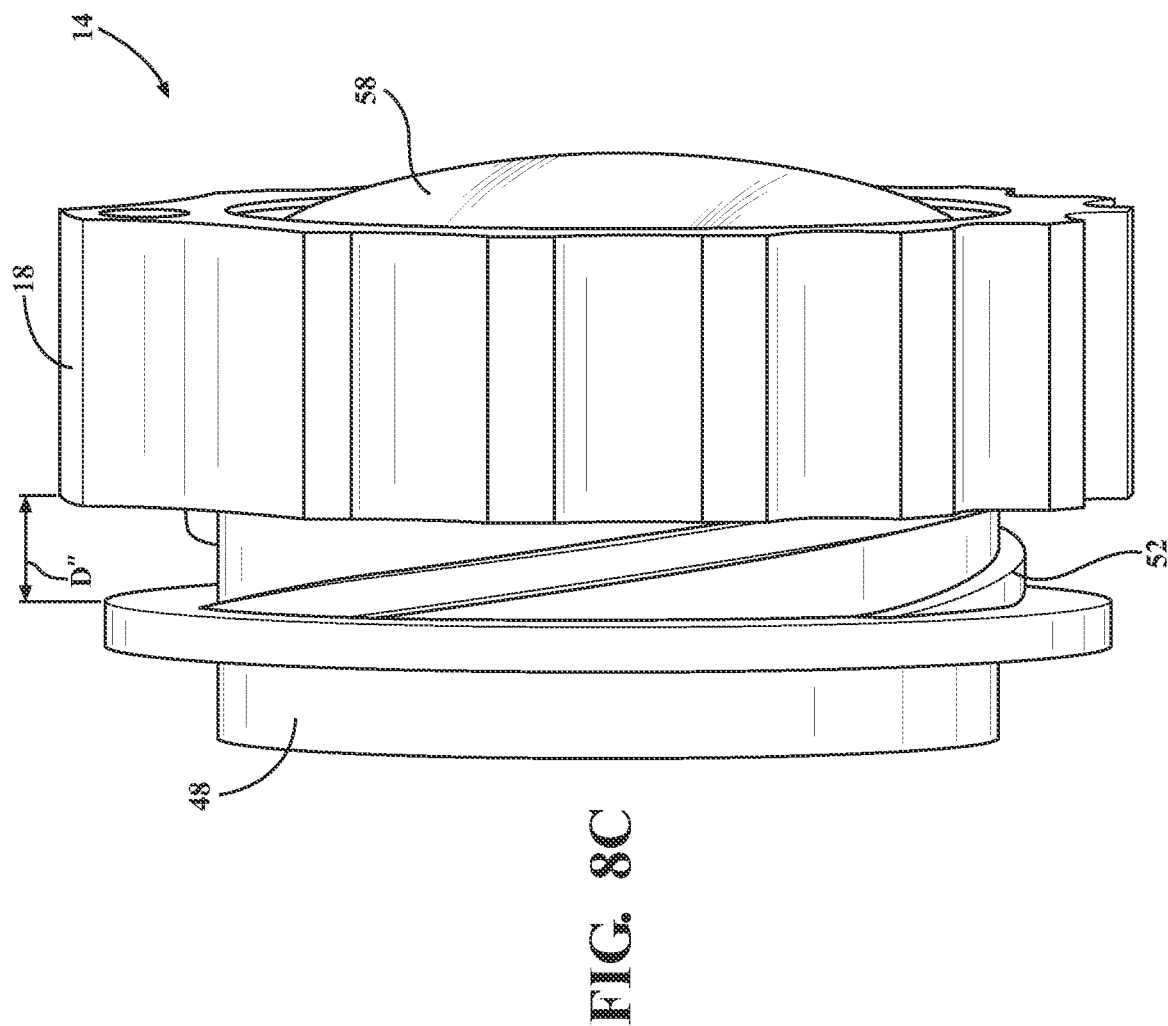
FIG. 8C is a perspective view of the second configuration of the lens assembly of FIGS. 3B and 4, illustrating the control member positioned at a third distance away from the housing.
Figure 9A:
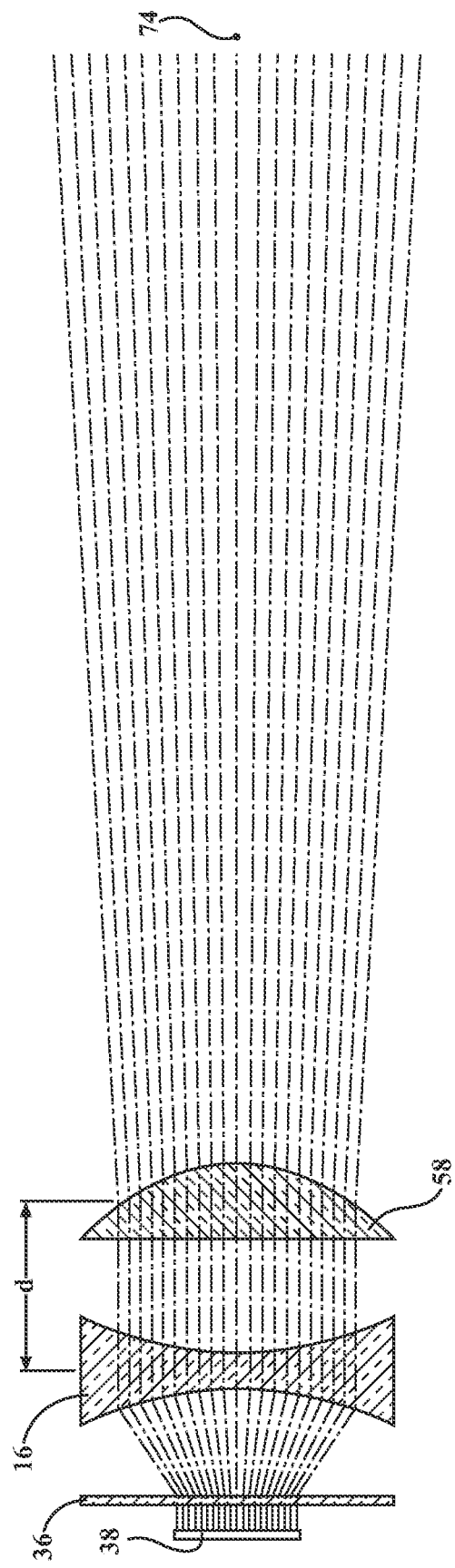
FIG. 9A is a schematic view of FIG. 8A illustrating an exemplary light pattern produced by the second configuration of the lens assembly including a first lens and a second lens when the control member is positioned at the first distance away from the housing.

Referring to FIGS. 8A-9C, an exemplary configuration of the lens assembly 14 is illustrated with the control member 18 at various positions relative to the housing 48 to illustrate the operation of the lens assembly 14. First, the housing 48 and the control member 18 are positioned at a first distance, D, from each other in FIG. 8A. Then, the wearer may utilize the grooves 56 of the control member 18 to manipulate position of the control member 18 relative to the housing 48. For example, when the control member 18 is coupled to the housing via a threaded connection, the user may twist/rotate the control member 18 which adjusts the distance between the control member 18 and the housing 48. FIG. 8B illustrates the control member 18 positioned at a second distance D' relative the housing 48. FIG. 8C illustrates the control member 18 positioned at a second distance D" relative the housing 48. The control member 18 may be manipulated to position of the control member 18 at any number of distances from the housing 48 based on the type of connection between the control member 18 and the housing 48. In turn, the manipulation of the control member 18 varies the distance between the first lens 16 and the second lens 58, as shown in FIGS. 9A-9C, which redirects or adjusts the light from the headlamp 12.

Figure 9B:
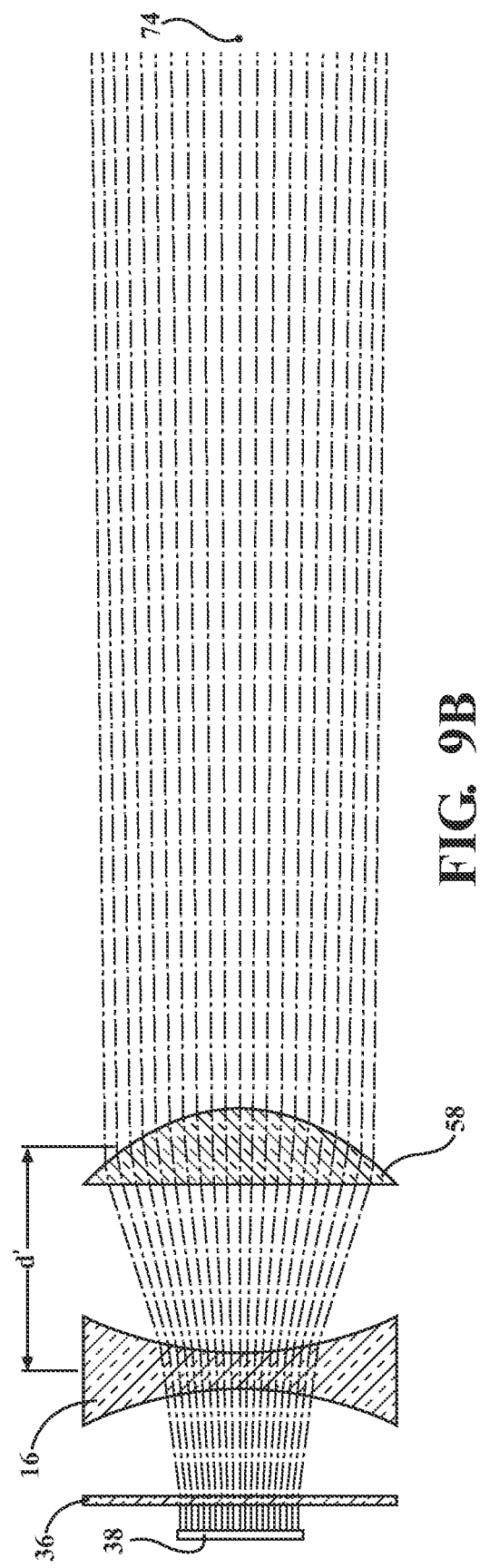
FIG. 9B is a schematic view of FIG. 8B illustrating an exemplary light pattern produced by the second configuration of the lens assembly including a first lens and a second lens when the control member is positioned at the second distance away from the housing.

Possible paths of the light from the headlamp 12 through the lens assembly 14 caused by the manipulation of the control member 18 by the wearer are depicted in FIGS. 9A-9C. The distance variation between the housing 48 and the control member 18 is illustrated as a distance D, a distance D', and a distance D" and may translate to the distance between the first lens 16 and the second lens 58 illustrated as a distance d, a distance d' and a distance d", respectively. In other words, the position of the second lens 58 is adjusted relative to the first lens 16. FIG. 8C illustrates further manipulation of the control member 18 translating to a distance variation of first lens 16 and the second 58 to a distance d" which is shown to redirect light towards a desired focal point 74 or to provide better visibility of the workspace. As illustrated in FIG. 9A-9C, light is emitted from the light source 38. The emitted light may pass through a lens 36 of the headlamp 12. The light may then pass through a lens 16 disposed within the coupling member 40 and/or the housing 48. The lens 16 may be configured to collect and/or direct the emitted light to through the lens assembly 14 toward a second lens, such as the lens 58 of the control member 18 of the lens assembly 14. The lens 58 may then direct the light toward in a direction based on the position of the control member 58 relative to the lens 16 of the coupling member 40 and/or the housing 48. The shape of the lenses 16, 58, and the distance between the lenses may dictate the direction and/or intensity of the light at the focal point 74.

Referring to FIG. 10, an exemplary configuration of path of the light from the headlamp 12 through the lens assembly 14C of FIG. 3C is illustrated. As illustrated in FIG. 10, light is emitted from the light source 38. The emitted light may then be collected by and/or pass through a lens 16 disposed within the coupling member 40C and/or the housing 48C. The lens 16 may be configured to direct the collected light to a fiber optic cable 19 configured to transmit the light along the length and/or the path of the fiber optic cable. The fiber optic cable 19 may comprise be configured to terminate at a lens, such as the lens 58C of the control member 18C of the lens assembly 14C. The lens 58C may then direct the light toward in a direction determine based on the position of the control member 18C.

The lens assembly 14 increases the efficiency, visibility, and sterility of a surgical procedure by enabling the wearer to redirect the light from the headlamp 12 during surgery without breaching the sterile barrier. Further, the wearer would not need to breach the sterile barrier to adjust the light by tilting the headlamp; rather the wearer would redirect the light from the headlamp 12 as described herein. Moreover, the lens assembly 14 is positioned such that the wearer's view of the surgical field, workspace, and the patient is unobstructed.

The above are directed to specific configurations of the system 5. It should be understood that the individual features of the different configurations of the system 5 may be combined to construct alternative configurations of the system 5.

It will be further appreciated that the terms "include," "includes," and "including" have the same meaning as the terms "comprise," "comprises," and "comprising."

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A wearable surgical garment for use with a surgical helmet having a headlamp, the wearable surgical garment comprising:
  a surgical fabric;
  a face shield coupled to the surgical fabric, the combination of the surgical fabric and the face shield defining an environment side and a wearer side and configured to provide a microbial barrier between a medical environment and a wearer; and
  a lens assembly positioned to be adjacent to the face shield and disposed on the environment side and configured to be aligned with the headlamp such that light emitted by the headlamp is transmitted through the lens assembly, the lens assembly comprising:
    a first lens,
    a second lens; and
    a control member, and
  wherein the control member is operatively coupled to the first lens such that the manipulation of the control member by the wearer on the environment side of the surgical garment adjusts a position of the second lens relative to the first lens to adjust a characteristic of the lens assembly.

2. The wearable surgical garment of claim 1, further comprising a coupling member at least partially disposed on the wearer side of the face shield.

3. The wearable surgical garment of claim 2, wherein the face shield is disposed between the coupling member and the lens assembly.

4. The wearable surgical garment of claim 3, wherein the face shield comprises an opening such that the light emitted by the headlamp is transmitted through the opening in the face shield and the coupling member.

5. The wearable surgical garment of claim 2, wherein the coupling member further comprises a mounting feature disposed on the wearer side of the face shield and configured to removably couple the headlamp to the coupling member.

6. The wearable surgical garment of claim 2, wherein the coupling member is ring-shaped.

7. The wearable surgical garment of claim 2, wherein the coupling member further comprises an attachment feature configured to be removably coupled to the lens assembly.

8. The wearable surgical garment of claim 2, wherein the coupling member is at least partially formed as a unitary component of the face shield.

9. The wearable surgical garment of claim 1, wherein the manipulation of the control member by the wearer on the environment side of the surgical garment to adjust the characteristic of the lens assembly comprises adjusting at least one of a direction and/or an intensity of the light emitted from the headlamp.

10. The wearable surgical garment of claim 1, wherein the first lens further comprises a film disposed on the first lens to filter the light emitted by the headlamp.

11. A protective apparel apparatus for use with a surgical helmet having a headlamp, the protective apparel apparatus comprising:
a wearable surgical garment defining an environment side and a wearer side, the surgical garment comprising a surgical fabric configured to provide a microbial barrier between a medical environment and a wearer;
a coupling member configured to be coupled to the headlamp; and
a lens assembly coupled to the surgical garment on the environment side and configured to be aligned with the headlamp, the lens assembly comprising:
a housing,
a first lens coupled to the housing,
a control member coupled to a second lens and the housing, and
wherein the control member is manipulatable by the wearer on the environment side of the surgical garment to adjust a position of the second lens relative the first lens to adjust a characteristic of the lens assembly;
wherein the housing of the lens assembly cooperates with the coupling member to align the first lens relative to the headlamp.

12. The protective apparel apparatus of claim 11, wherein the surgical garment further comprises a face shield.

13. The protective apparel apparatus of claim 11, wherein the coupling member further comprises an attachment feature configured to be removably coupled to the housing of the lens assembly.

14. The protective apparel apparatus of claim 13, wherein the attachment feature comprises a ferrous material.

15. The protective apparel apparatus of claim 11, wherein the control member comprises internal threads and wherein the housing comprises external threads whereby the internal threads of the control member are engageable with the external threads of the housing.

16. The protective apparel apparatus of claim 11, wherein the control member is manipulatable by the wearer by twisting the control member.

17. A protective apparel system comprising:
a surgical helmet to be worn over a head of a wearer, the surgical helmet comprising a headlamp;
a surgical garment configured to be at least partially disposed over the surgical helmet defining an environment side and a wearer side, said surgical garment comprising:
a surgical fabric configured to provide a microbial barrier between a medical environment and a wearer; and
a face shield coupled to the surgical fabric;
a lens assembly positioned to be adjacent the face shield and disposed on the environment side of the surgical garment, the lens assembly configured to be aligned with the headlamp such that light emitted by the headlamp is transmitted through the lens assembly, the lens assembly comprising:
a control member comprising a first lens, said control member coupled to the face shield; and
an adjustable portion configured to couple the control member to the face shield;
wherein said control member is configured such that manipulation of the control member by the wearer on the environment side of the face shield adjusts the position of the first lens relative to the face shield.

18. The protective apparel system of claim 17, wherein the adjustable portion is flexible and/or extendable/retractable to allow for a position and/or orientation of the control member to be manipulatable relative to the face shield and/or the headlamp.

* * * * *